US010433759B2

(12) United States Patent
Ahn et al.

(10) Patent No.: US 10,433,759 B2
(45) Date of Patent: Oct. 8, 2019

(54) MOBILE TERMINAL

(71) Applicant: LG ELECTRONICS INC., Seoul (KR)

(72) Inventors: Saeyoung Ahn, Seoul (KR); Dongsu Han, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 515 days.

(21) Appl. No.: 15/196,355

(22) Filed: Jun. 29, 2016

(65) Prior Publication Data

US 2017/0281044 A1 Oct. 5, 2017

(30) Foreign Application Priority Data

Apr. 5, 2016 (KR) .................... 10-2016-0041862

(51) Int. Cl.
*A61B 5/053* (2006.01)
*A61B 5/00* (2006.01)
*A61B 5/11* (2006.01)

(52) U.S. Cl.
CPC .......... *A61B 5/0537* (2013.01); *A61B 5/0022* (2013.01); *A61B 5/1116* (2013.01); *A61B 5/6898* (2013.01); *A61B 5/70* (2013.01); *A61B 5/742* (2013.01); *A61B 5/743* (2013.01); *A61B 5/746* (2013.01); *A61B 5/053* (2013.01); *A61B 5/4872* (2013.01); *A61B 5/744* (2013.01); *A61B 2560/0468* (2013.01)

(58) Field of Classification Search
CPC ......... A61B 5/0537; A61B 5/742; A61B 5/70; A61B 5/6898; A61B 5/4872; A61B 2560/0468; A61B 5/053
See application file for complete search history.

(56) References Cited

U.S. PATENT DOCUMENTS

| 6,188,925 | B1 * | 2/2001 | Kawanishi | A61B 5/0537 345/173 |
| 6,509,748 | B1 * | 1/2003 | Cheng | A61B 5/0537 324/692 |
| 6,551,257 | B1 * | 4/2003 | Sunako | A61B 5/0537 600/587 |

(Continued)

FOREIGN PATENT DOCUMENTS

| KR | 10-2005-0105783 A | 11/2005 |
| KR | 10-2005-0105822 A | 11/2005 |
| KR | 10-2015-0081735 A | 7/2015 |

*Primary Examiner* — Sean P Dougherty
(74) *Attorney, Agent, or Firm* — Birch, Stewart, Kolasch & Birch, LLP

(57) ABSTRACT

A mobile terminal including a terminal body having a metal case and defining an appearance of the mobile terminal; a display disposed on one surface of the terminal body; an antenna having a radiator provided on a functional area of the metal case, the antenna unit configured to execute wireless communication; a plurality of electrodes provided on one portion of the functional area and configured to generate current; and a controller configured to in response to a user grasping the mobile terminal such that the electrodes are in contact with the user, measure a body fat of the user based on voltages sensed by the electrodes, and display screen information on the display related to the determined body fat measurement.

19 Claims, 22 Drawing Sheets

(56) References Cited

U.S. PATENT DOCUMENTS

| | | | |
|---|---|---|---|
| 8,150,504 B2* | 4/2012 | Hwang | A61B 5/0059 600/473 |
| 2004/0002662 A1* | 1/2004 | Hjelt | A61B 5/0537 600/547 |
| 2005/0020936 A1* | 1/2005 | Lin | A61B 5/0537 600/547 |
| 2005/0228449 A1* | 10/2005 | Koyama | A61B 5/0537 607/1 |
| 2006/0020216 A1* | 1/2006 | Oishi | A61B 5/0205 600/500 |
| 2007/0293768 A1* | 12/2007 | Hwang | A61B 5/0059 600/476 |
| 2008/0071187 A1* | 3/2008 | Park | A61B 5/0537 600/547 |
| 2013/0012799 A1* | 1/2013 | Sasaki | A61B 5/0537 600/372 |
| 2015/0119654 A1* | 4/2015 | Martin | A61B 5/0059 600/301 |
| 2015/0156298 A1* | 6/2015 | Ikemoto | H04M 1/21 455/556.1 |
| 2016/0038037 A1* | 2/2016 | Kovacs | A61B 5/0205 600/301 |
| 2016/0113578 A1* | 4/2016 | Eom | A61B 5/681 600/547 |
| 2016/0324440 A1* | 11/2016 | Kim | A61B 5/6898 |
| 2016/0354036 A1* | 12/2016 | Jo | A61B 5/0537 |
| 2016/0357151 A1* | 12/2016 | Block | G04B 19/24 |
| 2016/0357282 A1* | 12/2016 | Block | G06F 1/163 |
| 2016/0357413 A1* | 12/2016 | Block | G06F 3/0482 |
| 2017/0020449 A1* | 1/2017 | Shim | A61B 5/7455 |

* cited by examiner (a)

100

(b)

A    B (a)

(b)

MOBILE TERMINAL

CROSS-REFERENCE TO RELATED APPLICATION

Pursuant to 35 U.S.C. § 119(a), this application claims the benefit of an earlier filing date of and the right of priority to Korean Application No. 10-2016-0041862, filed on Apr. 5, 2016, the contents of which are incorporated by reference herein in its entirety.

BACKGROUND OF THE INVENTION

1. Field of the Invention

This specification relates to a mobile terminal capable of measuring body fat.

2. Background of the Invention

A mobile terminal refers includes a battery and a display unit, outputs information on the display unit using power fed from the battery, and is portable by a user. The mobile terminal records and reproduces videos and displays graphic user interfaces (GUIs), and examples of the mobile terminal include a notebook, a portable phone, glasses and watch capable of displaying screen information, a game machine and the like.

As it becomes multifunctional, a mobile terminal can capture still images or moving images, play music or video files, play games, receive broadcast and the like, so as to be implemented as an integrated multimedia player. Many efforts include not only changes and improvement of structural components implementing a mobile terminal but also software improvement to support and improve functions of the terminal.

In recent time, a study on a function of collecting biometric data through sensors included in a mobile terminal is undergoing. Components for collecting biometric data are mounted to each area of the mobile terminal, which causes an increased volume of the mobile terminal. Also, since a human body has to be brought into contact with one area of the mobile terminal, a measurement is likely to be performed with improper posture, which makes it difficult to obtain a correct measurement result.

SUMMARY OF THE INVENTION

Therefore, an aspect of the detailed description is to provide a mobile terminal capable of measuring biometric data with improved accuracy.

To achieve these and other advantages and in accordance with the purpose of this specification, as embodied and broadly described herein, there is provided a mobile terminal, including a terminal body having a case made of a metal and defining appearance, a display unit disposed on one surface of the terminal body, an antenna unit having a radiator provided on a functional area of the metal case and configured to execute wireless communication, a body fat measurement module provided on one portion of the functional area and having a plurality of electrodes generating current, and a controller configured to generate biometric data based on voltages sensed by the electrodes, and control the display unit to output screen information related to the measurement of the biometric data while the body fat measurement module is activated.

In an embodiment disclosed herein, the radiator and the plurality of electrodes may be formed on a common portion of the functional area and selectively control a wireless communication function and a body fat measuring function.

A gap may be formed between the case and the antenna module. Accordingly, an additional space for mounting the electrodes may not be required, and the formation of the gap may minimize a degradation of wireless communication quality.

In an embodiment disclosed herein, the controller may control the plurality of electrodes to output a changed current value when an impedance value acquired by a current with a first frequency is not within a threshold value. Or, the mobile terminal may further include a sensor unit configured to detect at least one of a position and a movement of the mobile terminal, and a distance between the mobile terminal and a user, and the controller may control the body fat measurement module to execute a body fat measuring function when a change of the user's posture detected by the sensor unit satisfies a preset threshold range. Therefore, when the user's body is properly brought into contact with the electrodes and the user has good posture, the body fat measuring function can be executed and thus a more correct body fat measurement result can be provided.

According to an embodiment of the present invention, electrodes for a body fat measuring function may be formed on an area of a metal case with an antenna radiator, and thus an additional space for arranging the electrodes may not be required.

Also, electrodes may be located adjacent to sides (or edges) of a display unit, which may allow the display unit to provide screen information while the body fat measuring function is executed. Accordingly, a proper posture can be guided or measurement-related visual data can be provided during the execution of the body fat measuring function.

The body fat measuring function can be executed based on the user's measurement posture or a contact state of the user' body with the electrodes and the measurement result value can be calibrated based on changes detected during the measurement, thereby providing a more correct measurement result.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

BRIEF DESCRIPTION OF THE DRAWINGS

The accompanying drawings, which are included to provide a further understanding of the invention and are incorporated in and constitute a part of this specification, illustrate embodiments and together with the description serve to explain the principles of the invention.

In the drawings.

DETAILED DESCRIPTION OF THE INVENTION

Description will now be given in detail according to embodiments disclosed herein, with reference to the accompanying drawings. For the sake of brief description with reference to the drawings, the same or equivalent components may be provided with the same or similar reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

Although the terms first, second, etc. may be used herein to describe various elements, these elements should not be limited by these terms. These terms are generally only used to distinguish one element from another. When an element is referred to as being "connected with" another element, the element can be connected with the other element or intervening elements may also be present. In contrast, when an element is referred to as being "directly connected with" another element, there are no intervening elements present.

A singular representation may include a plural representation unless it represents a definitely different meaning from the context. Terms such as "include" or "has" are used herein and should be understood that they are intended to indicate an existence of features, numbers, steps, functions, several components, or combinations thereof, disclosed in the specification, and it is also understood that greater or fewer features, numbers, steps, functions, several components, or combinations thereof may likewise be utilized.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, slate PCs, tablet PCs, ultra books, wearable devices (for example, smart watches, smart glasses, head mounted displays (HMDs)), and the like.

By way of non-limiting example only, further description will be made with reference to particular types of mobile terminals. However, such teachings apply equally to other types of terminals, such as those types noted above. In addition, these teachings may also be applied to stationary terminals such as digital TV, desktop computers, digital signage, and the like.

Figure 1A:
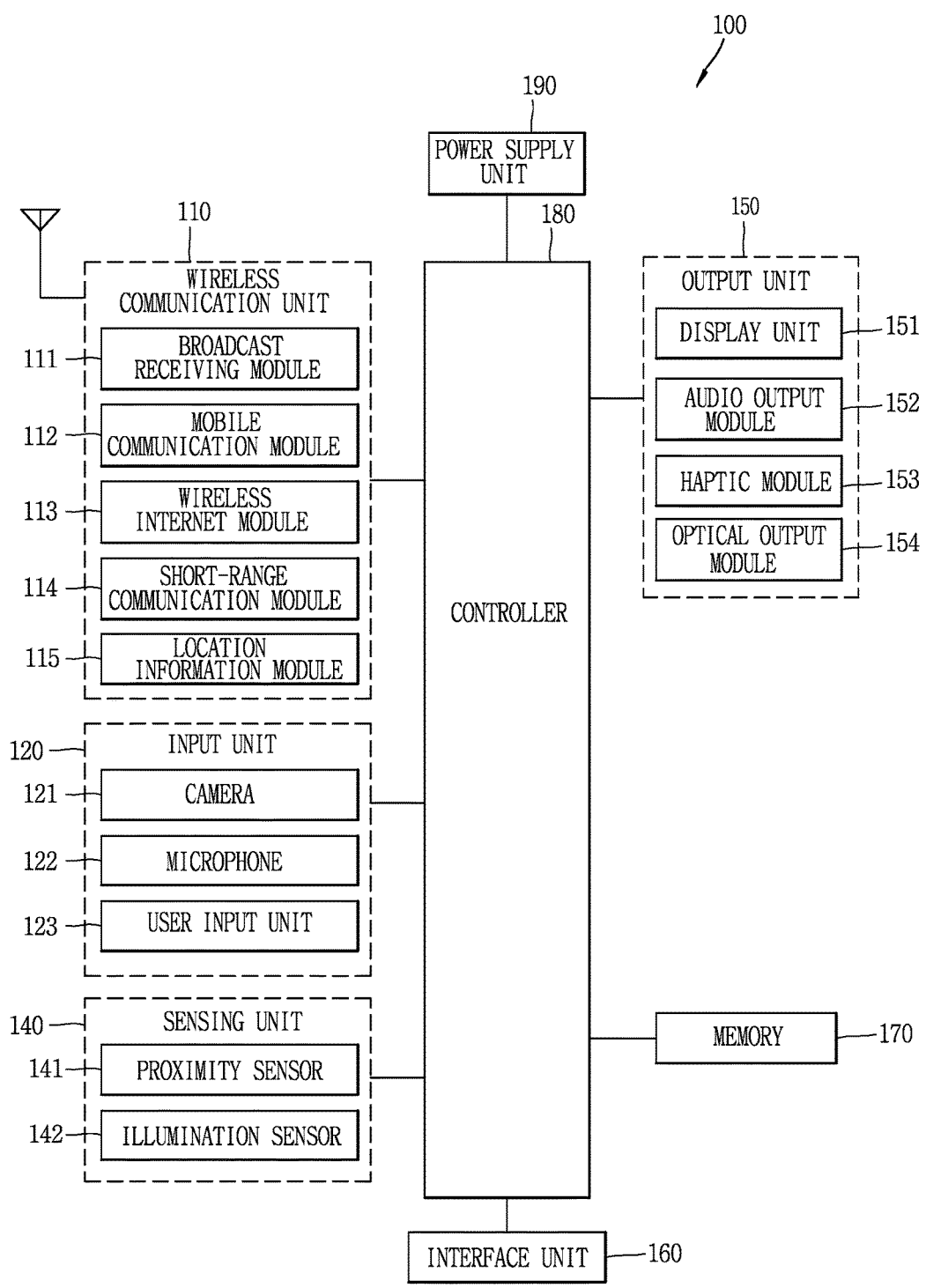
FIG. 1A is a block diagram of a mobile terminal in accordance with one embodiment of the present invention.
Figure 1B:
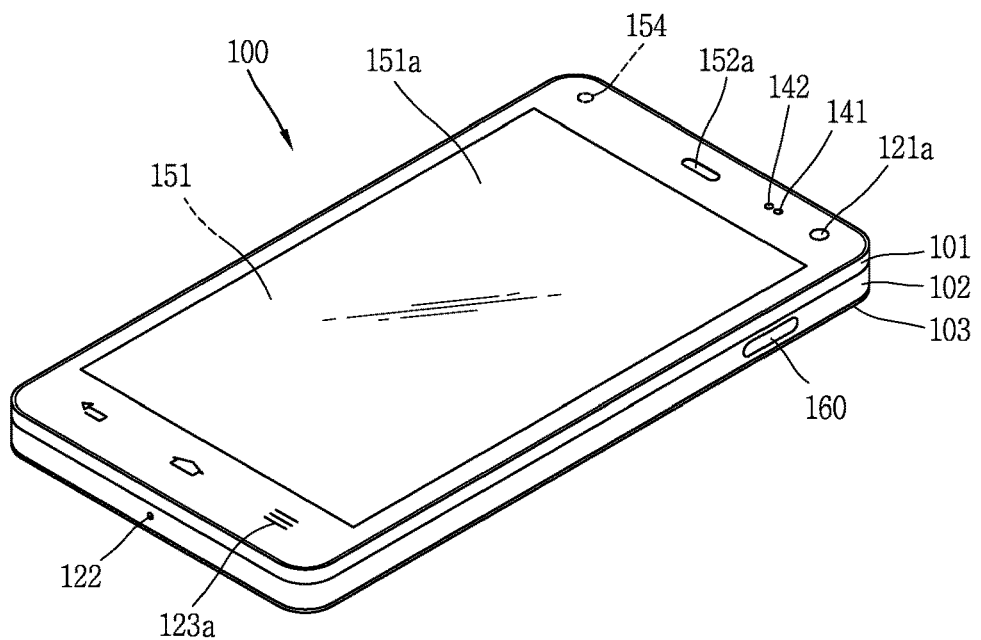
FIGS. 1B and 1C are conceptual views illustrating one example of the mobile terminal, viewed from different directions.
Figure 1C:
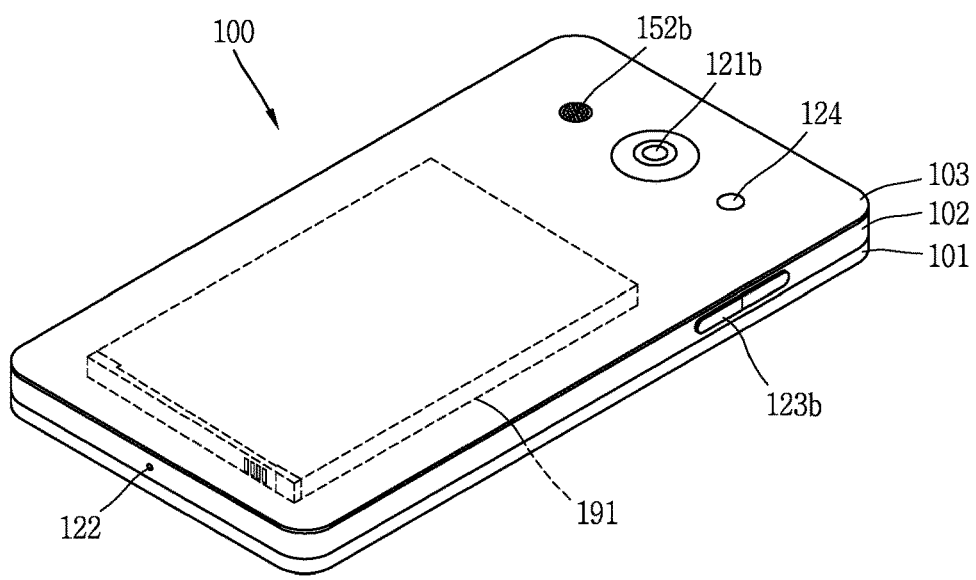

Reference is now made to FIGS. 1A-1C, where FIG. 1A is a block diagram of a mobile terminal in accordance with the present disclosure, and FIGS. 1B and 1C are conceptual views of one example of the mobile terminal, viewed from different directions. The mobile terminal 100 is shown having components such as a wireless communication unit 110, an input unit 120, a sensing unit 140, an output unit 150, an interface unit 160, a memory 170, a controller 180, and a power supply unit 190. Implementing all of the illustrated components is not a requirement, and that greater or fewer components may alternatively be implemented.

In more detail, the wireless communication unit 110 typically includes one or more modules which permit communications such as wireless communications between the mobile terminal 100 and a wireless communication system, communications between the mobile terminal 100 and another mobile terminal, communications between the mobile terminal 100 and an external server. Further, the wireless communication unit 110 typically includes one or more modules which connect the mobile terminal 100 to one or more networks.

The wireless communication unit 110 includes one or more of a broadcast receiving module 111, a mobile communication module 112, a wireless Internet module 113, a short-range communication module 114, and a location information module 115. The input unit 120 includes a camera 121 or an image input unit for obtaining images or video, a microphone 122, which is one type of audio input device for inputting an audio signal, and a user input unit 123 (for example, a touch key, a mechanical key, and the like) for allowing a user to input information. Data (for example, audio, video, image, and the like) is obtained by the input unit 120 and may be analyzed and processed according to user commands.

The sensing unit 140 is typically implemented using one or more sensors configured to sense internal information of the mobile terminal, the surrounding environment of the mobile terminal, user information, and the like. For example, the sensing unit 140 may include at least one of a proximity sensor 141, an illumination sensor 142, a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like). The mobile terminal disclosed herein may be configured to utilize information obtained from one or more sensors of the sensing unit 140, and combinations thereof.

The output unit 150 is typically configured to output various types of information, such as audio, video, tactile output, and the like. The output unit 150 is shown having at least one of a display unit 151, an audio output module 152, a haptic module 153, and an optical output module 154. The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 typically functions to control overall operation of the mobile terminal 100, in addition to the operations associated with the application programs. The controller 180 can provide or process information or functions appropriate for a user by processing signals, data, information and the like, which are input or output by the aforementioned various components, or activating application programs stored in the memory 170.

Also, the controller 180 controls some or all of the components illustrated in FIG. 1A according to the execution of an application program that have been stored in the memory 170. In addition, the controller 180 can control at least two of those components included in the mobile terminal to activate the application program.

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

At least part of the components may cooperatively operate to implement an operation, a control or a control method of a mobile terminal according to various embodiments disclosed herein. Also, the operation, the control or the control method of the mobile terminal may be implemented on the mobile terminal by an activation of at least one application program stored in the memory 170.

Hereinafter, description will be given in more detail of the aforementioned components with reference to FIG. 1A, prior to describing various embodiments implemented through the mobile terminal 100. First, regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some embodiments, two or more broadcast receiving modules 111 may be utilized to facilitate simultaneously receiving of two or more broadcast channels, or to support switching among broadcast channels.

The mobile communication module 112 can transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (for example, Global System for Mobile Communication (GSM), Code Division Multi Access (CDMA), CDMA2000 (Code Division Multi Access 2000), EV-DO (Enhanced Voice-Data Optimized or Enhanced Voice-Data Only), Wideband CDMA (WCDMA), High Speed Downlink Packet access (HSDPA), HSUPA (High Speed Uplink Packet Access), Long Term Evolution (LTE), LTE-A (Long Term Evolution-Advanced), and the like). Examples of wireless signals transmitted and/or received via the mobile communication module 112 include audio call signals, video (telephony) call signals, or various formats of data to support communication of text and multimedia messages.

The wireless Internet module 113 is configured to facilitate wireless Internet access. This module may be internally or externally coupled to the mobile terminal 100. The wireless Internet module 113 may transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA (High Speed Uplink Packet Access), Long Term Evolution (LTE), LTE-A (Long Term Evolution-Advanced), and the like. The wireless Internet module 113 may transmit/receive data according to one or more of such wireless Internet technologies, and other Internet technologies as well.

In some embodiments, when the wireless Internet access is implemented according to, for example, WiBro, HSDPA, HSUPA, GSM, CDMA, WCDMA, LTE, LTE-A and the like, as part of a mobile communication network, the wireless Internet module 113 performs such wireless Internet access. As such, the Internet module 113 may cooperate with, or function as, the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the mobile terminal 100 and a wireless communication system, communications between the mobile terminal 100 and another mobile terminal 100, or communications between the mobile terminal and a network where another mobile terminal 100 (or an external server) is located, via wireless area networks. One example of the wireless area networks is a wireless personal area networks.

Here, another mobile terminal (which may be configured similarly to mobile terminal 100) may be a wearable device, for example, a smart watch, a smart glass or a head mounted display (HMD), which can exchange data with the mobile terminal 100 (or otherwise cooperate with the mobile terminal 100). The short-range communication module 114 may sense or recognize the wearable device, and permit communication between the wearable device and the mobile terminal 100. In addition, when the sensed wearable device is a device which is authenticated to communicate with the mobile terminal 100, the controller 180, for example, may cause transmission of at least part of data processed in the mobile terminal 100 to the wearable device via the short-range communication module 114.

Hence, a user of the wearable device may use the data processed in the mobile terminal 100 on the wearable device. For example, when a call is received in the mobile terminal 100, the user may answer the call using the wearable device. Also, when a message is received in the mobile terminal 100, the user can check the received message using the wearable device.

The location information module 115 is generally configured to detect, calculate, derive or otherwise identify a position (or current position) of the mobile terminal. As an example, the location information module 115 includes a Global Position System (GPS) module, a Wi-Fi module, or both. For example, when the mobile terminal uses a GPS module, a position of the mobile terminal may be acquired using a signal sent from a GPS satellite. As another example, when the mobile terminal uses the Wi-Fi module, a position of the mobile terminal can be acquired based on information related to a wireless access point (AP) which transmits or receives a wireless signal to or from the Wi-Fi module. If desired, the location information module 115 may alternatively or additionally function with any of the other modules of the wireless communication unit 110 to obtain data related to the position of the mobile terminal. The location information module 115 is a module used for acquiring the position (or the current position) and may not be limited to a module for directly calculating or acquiring the position of the mobile terminal.

The input unit 120 may be configured to permit various types of inputs (information or signals) to the mobile terminal 100. Examples of such inputs include audio, image, video, data, and user input. Image and video input is often obtained using one or more cameras 121. Such cameras 121 may process image frames of still pictures or video obtained by image sensors in a video or image capture mode. The processed image frames can be displayed on the display unit 151 or stored in memory 170. In addition, the cameras 121 may be arranged in a matrix configuration to permit a plurality of images having various angles or focal points to be input to the mobile terminal 100. Also, the cameras 121 may be located in a stereoscopic arrangement to acquire left and right images for implementing a stereoscopic image.

The microphone 122 processes an external audio signal into electric audio (sound) data. The processed audio data can be processed in various manners according to a function (or an application program) being executed in the mobile terminal 100. If desired, the microphone 122 may include assorted noise removing algorithms to remove unwanted noise generated in the course of receiving the external audio signal.

The user input unit 123 is a component that permits input by a user. Such user input may enable the controller 180 to control operation of the mobile terminal 100. The user input unit 123 may include one or more of a mechanical input element (for example, a mechanical key, a button located on a front and/or rear surface or a side surface of the mobile terminal 100, a dome switch, a jog wheel, a jog switch, and the like), or a touch-sensitive input element, among others. As one example, the touch-sensitive input element may be a virtual key, a soft key or a visual key, which is displayed on a touch screen through software processing, or a touch key which is located on the mobile terminal at a location that is other than the touch screen. Further, the virtual key or the visual key may be displayed on the touch screen in various shapes, for example, graphic, text, icon, video, or a combination thereof.

The sensing unit 140 is generally configured to sense one or more of internal information of the mobile terminal, surrounding environment information of the mobile terminal, user information, or the like, and generate a corresponding sensing signal. The controller 180 generally cooperates with the sending unit 140 to control operation of the mobile terminal 100 or execute data processing, a function or an operation associated with an application program installed in the mobile terminal based on the sensing signal. The sensing unit 140 may be implemented using any of a variety of sensors, some of which will now be described in more detail.

The proximity sensor 141 refers to a sensor to sense presence or absence of an object approaching a surface, or an object located near a surface, by using an electromagnetic field, infrared rays, or the like without a mechanical contact. The proximity sensor 141 may be arranged at an inner region of the mobile terminal covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this instance, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, distance, direction, speed, time, position, moving status, and the like). In general, controller 180 processes data corresponding to proximity touches and proximity touch patterns sensed by the proximity sensor 141, and cause output of visual information on the touch screen. In addition, the controller 180 can control the mobile terminal 100 to execute different operations or process different data (or information) according to whether a touch with respect to a point on the touch screen is either a proximity touch or a contact touch.

A touch sensor can sense a touch (or a touch input) applied to the touch screen, such as display unit 151, using any of a variety of touch methods. Examples of such touch methods include a resistive type, a capacitive type, an infrared type, and a magnetic field type, among others. As one example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched region, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 180. Accordingly, the controller 180 can sense which region of the display unit 151 has been touched. Here, the touch controller may be a component separate from the controller 180, the controller 180, and combinations thereof.

In addition, the controller 180 can execute the same or different controls according to a type of touch object that touches the touch screen or a touch key provided in addition to the touch screen. Whether to execute the same or different control according to the object which provides a touch input may be decided based on a current operating state of the mobile terminal 100 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The controller 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121, which has been depicted as a component of the input unit 120, typically includes at least one a camera sensor (CCD, CMOS etc.), a photo sensor (or image sensors), and a laser sensor. Implementing the camera 121 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the mobile terminal 100. For example, the display unit 151 may display execution screen information of an application program executing at the mobile terminal 100 or user interface (UI) and graphic user interface (GUI) information in response to the execution screen information.

Also, the display unit 151 may be implemented as a stereoscopic display unit for displaying stereoscopic images. A typical stereoscopic display unit may employ a stereoscopic display scheme such as a stereoscopic scheme (a glass scheme), an auto-stereoscopic scheme (glassless scheme), a projection scheme (holographic scheme), or the like.

Referring now to FIGS. 1B and 1C, the mobile terminal 100 is described with reference to a bar-type terminal body. However, the mobile terminal 100 may alternatively be implemented in any of a variety of different configurations. Examples of such configurations include watch-type, clip-type, glasses-type, or as a folder-type, flip-type, slide-type, swing-type, and swivel-type in which two and more bodies are combined with each other in a relatively movable manner, and combinations thereof. Discussion herein will often relate to a particular type of mobile terminal. However, such teachings with regard to a particular type of mobile terminal will generally apply to other types of mobile terminals as well.

The mobile terminal 100 will generally include a case (for example, frame, housing, cover, and the like) forming the appearance of the terminal. In this embodiment, the case is formed using a front case 101 and a rear case 102. Various electronic components are incorporated into a space formed between the front case 101 and the rear case 102. At least one middle case may be additionally positioned between the front case 101 and the rear case 102.

The display unit 151 is shown located on the front side of the terminal body to output information. As illustrated, a window 151a of the display unit 151 may be mounted to the front case 101 to form the front surface of the terminal body together with the front case 101.

In some embodiments, electronic components may also be mounted to the rear case 102. Examples of such electronic components include a detachable battery 191, an identification module, a memory card, and the like. Rear cover 103 is shown covering the electronic components, and this cover may be detachably coupled to the rear case 102. Therefore, when the rear cover 103 is detached from the rear case 102, the electronic components mounted to the rear case 102 are externally exposed.

As illustrated, when the rear cover 103 is coupled to the rear case 102, a side surface of the rear case 102 is partially exposed. In some cases, upon the coupling, the rear case 102 may also be completely shielded by the rear cover 103. In some embodiments, the rear cover 103 may include an opening for externally exposing a camera 121b or an audio output module 152b.

The cases 101, 102, 103 may be formed by injection-molding synthetic resin or may be formed of a metal, for example, stainless steel (STS), aluminum (Al), titanium (Ti), or the like. As an alternative to the example in which the plurality of cases form an inner space for accommodating components, the mobile terminal 100 may be configured such that one case forms the inner space. In this example, a mobile terminal 100 having a uni-body is formed so synthetic resin or metal extends from a side surface to a rear surface.

If desired, the mobile terminal 100 may include a waterproofing unit for preventing introduction of water into the terminal body. For example, the waterproofing unit may include a waterproofing member which is located between the window 151a and the front case 101, between the front case 101 and the rear case 102, or between the rear case 102 and the rear cover 103, to hermetically seal an inner space when those cases are coupled.

The mobile terminal 100 may include a display unit 151, first and second audio output module 152a and 152b, a proximity sensor 141, an illumination sensor 142, an optical output module 154, first and second cameras 121a and 121b, first and second manipulation units 123a and 123b, a microphone 122, an interface unit 160, and the like.

Hereinafter, as illustrated in FIGS. 1B and 1C, description will be given of the exemplary mobile terminal 100 in which the front surface of the terminal body is shown having the display unit 151, the first audio output module 152a, the proximity sensor 141, the illumination sensor 142, the optical output module 154, the first camera 121a, and the first manipulation unit 123a, the side surface of the terminal body is shown having the second manipulation unit 123b, the microphone 122, and the interface unit 160, and the rear surface of the terminal body is shown having the second audio output module 152b and the second camera 121b.

However, those components may not be limited to the arrangement. Some components may be omitted or rearranged or located on different surfaces. For example, the first manipulation unit 123a may be located on another surface of the terminal body, and the second audio output module 152b may be located on the side surface of the terminal body other than the rear surface of the terminal body.

The display unit 151 outputs information processed in the mobile terminal 100. For example, the display unit 151 may display execution screen information of an application program executing at the mobile terminal 100 or user interface (UI) and graphic user interface (GUI) information in response to the execution screen information.

The display unit 151 may be implemented using one or more suitable display devices. Examples of such suitable display devices include a liquid crystal display (LCD), a thin film transistor-liquid crystal display (TFT-LCD), an organic light emitting diode (OLED), a flexible display, a 3-dimensional (3D) display, an e-ink display, and combinations thereof.

The display unit 151 may be implemented using two display devices, which can implement the same or different display technology. For instance, a plurality of the display units 151 may be arranged on one side, either spaced apart from each other, or these devices may be integrated, or these devices may be arranged on different surfaces.

The display unit 151 may also include a touch sensor which senses a touch input received at the display unit. When a touch is input to the display unit 151, the touch sensor may be configured to sense this touch and the controller 180, for example, may generate a control command or other signal corresponding to the touch. The content which is input in the touching manner may be a text or numerical value, or a menu item which can be indicated or designated in various modes.

The touch sensor may be configured in a form of a film having a touch pattern, disposed between the window 151a and a display on a rear surface of the window 151a, or a metal wire which is patterned directly on the rear surface of the window 151a. Alternatively, the touch sensor may be integrally formed with the display. For example, the touch sensor may be disposed on a substrate of the display or within the display.

The display unit 151 may also form a touch screen together with the touch sensor. Here, the touch screen may serve as the user input unit 123 (see FIG. 1A). Therefore, the touch screen may replace at least some of the functions of the first manipulation unit 123a.

The first audio output module 152a may be implemented in the form of a receiver for transferring call sounds to a user's ear and the second audio output module 152b may be implemented in the form of a loud speaker to output alarm sounds, multimedia audio reproduction, and the like.

The window 151a of the display unit 151 will typically include an aperture to permit audio generated by the first audio output module 152a to pass. One alternative is to allow audio to be released along an assembly gap between the structural bodies (for example, a gap between the window 151a and the front case 101). In this instance, a hole independently formed to output audio sounds may not be seen or is otherwise hidden in terms of appearance, thereby further simplifying the appearance and manufacturing of the mobile terminal 100.

The optical output module 154 can be configured to output light for indicating an event generation. Examples of such events include a message reception, a call signal reception, a missed call, an alarm, a schedule alarm, an email reception, information reception through an application, and the like. When a user has checked a generated event, the controller 180 can control the optical output module 154 to stop the light output.

The first camera 121a can process image frames such as still or moving images obtained by the image sensor in a capture mode or a video call mode. The processed image frames can then be displayed on the display unit 151 or stored in the memory 170.

The first and second manipulation units 123a and 123b are examples of the user input unit 123, which may be manipulated by a user to provide input to the mobile terminal 100. The first and second manipulation units 123a and 123b may also be commonly referred to as a manipulating portion, and may employ any tactile method that allows the user to perform manipulation such as touch, push, scroll, or the like. The first and second manipulation units 123a and 123b may also employ any non-tactile method that allows the user to perform manipulation such as proximity touch, hovering, or the like.

FIG. 1B illustrates the first manipulation unit 123a as a touch key, but possible alternatives include a mechanical key, a push key, a touch key, and combinations thereof. Input received at the first and second manipulation units 123a and 123b may be used in various ways. For example, the first manipulation unit 123a may be used by the user to provide an input to a menu, home key, cancel, search, or the like, and the second manipulation unit 123b may be used by the user to provide an input to control a volume level being output from the first or second audio output modules 152a or 152b, to switch to a touch recognition mode of the display unit 151, or the like.

As another example of the user input unit 123, a rear input unit may be located on the rear surface of the terminal body. The rear input unit can be manipulated by a user to provide input to the mobile terminal 100. The input may be used in a variety of different ways. For example, the rear input unit may be used by the user to provide an input for power on/off, start, end, scroll, control volume level being output from the first or second audio output modules 152a or 152b, switch to a touch recognition mode of the display unit 151, and the like. The rear input unit may be configured to permit touch input, a push input, or combinations thereof.

The rear input unit may be located to overlap the display unit 151 of the front side in a thickness direction of the terminal body. As one example, the rear input unit may be located on an upper end portion of the rear side of the terminal body such that a user can easily manipulate it using a forefinger when the user grabs the terminal body with one hand. Alternatively, the rear input unit can be positioned at most any location of the rear side of the terminal body.

When the rear input unit is provided on the rear surface of the terminal body, new types of user interfaces using the rear input unit can be implemented. Embodiments that include the aforementioned touch screen or the rear input unit may implement some or all of the functionality of the first manipulation unit 123a provided on the front surface of the terminal body. As such, in situations where the first manipulation unit 123a is omitted from the front side, the display unit 151 can have a larger screen.

As a further alternative, the mobile terminal 100 may include a finger scan sensor which scans a user's fingerprint. The controller 180 can then use fingerprint information sensed by the finger scan sensor as part of an authentication procedure. The finger scan sensor may also be installed in the display unit 151 or implemented in the user input unit 123.

The microphone 122 is shown located at an end of the mobile terminal 100, but other locations are possible. If desired, multiple microphones may be implemented, with such an arrangement permitting the receiving of stereo sounds.

The interface unit 160 may serve as a path allowing the mobile terminal 100 to interface with external devices. For example, the interface unit 160 may include one or more of a connection terminal for connecting to another device (for example, an earphone, an external speaker, or the like), a port for near field communication (for example, an Infrared Data Association (IrDA) port, a Bluetooth port, a wireless LAN port, and the like), or a power supply terminal for supplying power to the mobile terminal 100. The interface unit 160 may be implemented in the form of a socket for accommodating an external card, such as Subscriber Identification Module (SIM), User Identity Module (UIM), or a memory card for information storage.

The second camera 121b is shown located at the rear side of the terminal body and includes an image capturing direction that is substantially opposite to the image capturing direction of the first camera unit 121a. The second camera 121b can include a plurality of lenses arranged along at least one line. The plurality of lenses may also be arranged in a matrix configuration. The cameras may be referred to as an "array camera." When the second camera 121b is implemented as an array camera, images may be captured in various manners using the plurality of lenses and images with better qualities.

A flash 124 is shown adjacent to the second camera 121b. When an image of a subject is captured with the camera 121b, the flash 124 may illuminate the subject. The second audio output module 152b can be located on the terminal body. The second audio output module 152b may implement stereophonic sound functions in conjunction with the first audio output module 152a, and may be also used for implementing a speaker phone mode for call communication.

At least one antenna for wireless communication may be located on the terminal body. The antenna may be installed in the terminal body or formed by the case. For example, an antenna which configures a part of the broadcast receiving module 111 may be retractable into the terminal body. Alternatively, an antenna may be formed using a film attached to an inner surface of the rear cover 103, or a case that includes a conductive material.

A power supply unit 190 for supplying power to the mobile terminal 100 may include a battery 191, which is mounted in the terminal body or detachably coupled to an outside of the terminal body. The battery 191 may receive power via a power source cable connected to the interface unit 160. Also, the battery 191 can be recharged in a wireless manner using a wireless charger. Wireless charging may be implemented by magnetic induction or electromagnetic resonance.

The rear cover 103 is shown coupled to the rear case 102 for shielding the battery 191, to prevent separation of the battery 191, and to protect the battery 191 from an external impact or from foreign material. When the battery 191 is detachable from the terminal body, the rear case 103 may be detachably coupled to the rear case 102.

An accessory for protecting an appearance or assisting or extending the functions of the mobile terminal 100 can also be provided on the mobile terminal 100. As one example of an accessory, a cover or pouch for covering or accommodating at least one surface of the mobile terminal 100 may be provided. The cover or pouch may cooperate with the display unit 151 to extend the function of the mobile terminal 100. Another example of the accessory is a touch pen for assisting or extending a touch input to a touch screen.

Hereinafter, description will be given of embodiments related to a control method which can be implemented in the mobile terminal having such configuration, with reference to the accompanying drawings. It will be obvious to those skilled in the art that the present invention can be specified into other specific forms without departing from the scope and essential features of the present invention.

The mobile terminal disclosed herein includes a body fat measurement module that collects biometric data of a user. The body fat measurement module may collect body fat information and the like based on an impedance value according to a current flowing along the user's body when the user's body is brought into contact with it. Hereinafter, description will be given in detail of a structure of the body fat measurement module and related control methods according to various embodiments.

Figure 2A:
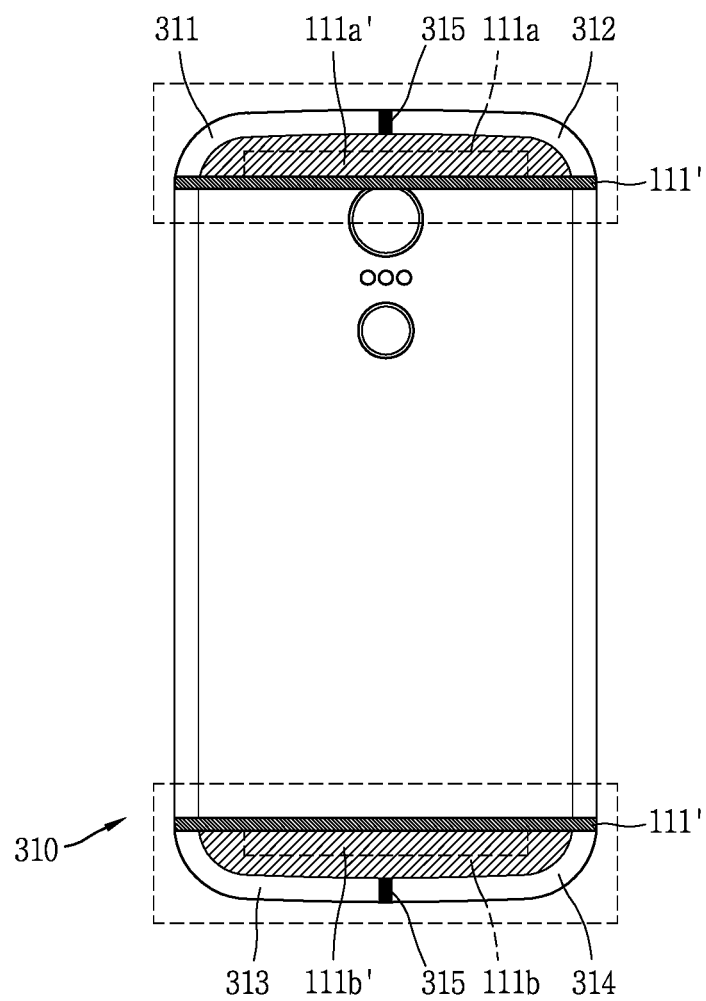
FIG. 2A is a conceptual view illustrating a structure of body fat measurement module included in a mobile terminal in accordance with one embodiment of the present invention.

FIGS. 2A to 2D are conceptual views illustrating a structure of a body fat measurement module and a method of measuring biometric data in accordance with one embodiment of the present invention. In particular, FIG. 2A is a conceptual view illustrating an arrangement of the body fat measurement module 310 according to the one embodiment.

The body fat measurement module 310 includes a plurality of electrodes. For example, the body fat measurement module 310 includes first to fourth electrodes 311, 312, 313 and 314. The four electrodes supply currents to flow along a user's body, and collect the user's body fat information based on an impedance value using a difference of voltages passed through one area of the body. The present invention is not limited to the number of electrodes. For example, two electrodes may alternatively be used.

Conductivities of adipose and muscles constructing the user's body are measured in different manners. A lean body (lean body mass or fat-free mass) contains the most of water within the body and has a conductive property so that a current flows well therealong when a weak current is supplied to the body. Further, body fat (or body fat mass) rarely contains water and has a non-conductive property so that a current does not flow well therealong. A body weight is decided by the sum of the body fat mass and the fat-free mass, and the fat-free mass is the sum of a muscle mass and a mineral mass.

Therefore, even when the same current flows, a difference of voltage values measured is caused according to a mass of fat and a mass of muscles contained in one area of the body along which the current flows. The adipose (fat) has a non-conductive property such that a current does not flow well therealong and has a high impedance value. The muscle has the same property as a conductor along which a current flows well and has a low impedance value. That is, the controller 180 can acquire a body fat measurement result of the body using the impedance values.

At least one area of the case which includes the front case 101, the rear case 102 and the rear cover 103 of the mobile terminal and defines an outer surface of a terminal body may be made of a metal. The first to fourth electrodes 311, 312, 313 and 314 are disposed at both end portions on the outer surface of the terminal body of the mobile terminal 100 to supply a current to the user's body. The display unit 151 may be disposed on one surface of the terminal body and the first to fourth electrodes 311, 312, 313 and 314 may be provided on areas adjacent to sides (edges) of the display unit 151.

The first to fourth electrodes 311, 312, 313 and 314 which are disposed on the case are contactable with a part of the user's body. The first to fourth electrodes 311, 312, 313 and 314 may be made of a clad metal. The clad metal is highly resistant to corrosion and has conductivity. By use of the clad metal, a surface corrosion can be prevented even without a coating layer. By forming the plurality of electrodes using the clad metal, damages on the plurality of electrodes caused due to the corrosion can be minimized even though they are disposed on the outer surface of the terminal body to be brought into contact with the user's body.

An area of the case may be implemented as radiators of first and second antenna units 111a and 111b. As illustrated in FIG. 2A, slit structures 111' are provided to divide the radiators forming the first and second antenna units 111a and 111b from the other area of the case. Each of the first and second antenna units 111a and 111b may include the radiator and an antenna module disposed adjacent to the area of the case forming the radiator.

According to this embodiment, the first and second antenna units 111a and 111b are disposed on both end portions of the terminal body, respectively. The first and second antenna units 111a and 111b are configured to transmit and receive different types of wireless signals. The first and second antenna units 111a and 111b are adjacent to the outer surface of the terminal body, respectively, and disposed in parallel to the both end portions of the display unit 151. The first and second antenna units 111a and 111b include first and second radiators 111a' and 111b', respectively, which are formed on an area of the case. In one embodiment, the first and second radiators 111a' and 1111b' are provided on an area of the rear cover 103. The first and second radiators 111a' and 111b' and the other area of the rear cover 103 are insulated from each other by the slit structures 111'.

The first and second electrodes 311 and 312 are provided on side surfaces of the terminal body which are adjacent to the first antenna unit 111a. The first to fourth electrodes 311, 312, 313 and 314 may share one area of the case which is formed of the metal together with the first and second radiators 111a' and 111b'. That is, the first and second radiators 111a' and 111b' and the first to fourth electrodes 311, 312, 313 and 314 are disposed on the one area of the case.

An insulating member 315 is interposed between the first and second electrodes 311 and 312. The first and second electrodes 311 and 312 may be formed in the same shape but the present invention is not limited to this. That is, the first and second electrodes 311 and 312 may have different lengths and shapes from each other.

In addition, the third and fourth electrodes 313 and 314 are provided on a side surface of the terminal body which is adjacent to the second antenna unit 111b. The third and fourth electrodes 313 and 314 are arranged in series with the insulating member 315 interposed therebetween. The third and fourth electrodes 313 and 314 may have the same shape but the present invention is not limited to this.

That is, the third and fourth electrodes 313 and 314 may have different lengths and shapes from each other. Insulating structures are disposed among the first to fourth electrodes 311, 312, 313 and 314 to avoid an electric connection. The first to fourth electrodes 311, 312, 313 and 314 form one area of the rear case 102 or the rear cover 103.

The body fat measurement module 310 includes a control unit that is connected to the first to fourth electrodes 311, 312, 313 and 314 and calculates body fat information. The control unit of the body fat measurement module 310 is configured to be independent of the antenna modules of the first and second antenna units 111a and 111b. Therefore, the operations of the first and second antenna units 111a and 111b and the operation of the body fat measurement module 310 are controlled in the independent manner.

The body fat measurement module 310 according to this embodiment includes the four electrodes but may alternatively include two electrodes. When the body fat measurement module 310 includes such two electrodes, the body fat information may be calculated through a step of correcting (compensating for) an error. Or, when an impedance value is measured using the two electrodes, a resistance of the body relatively increases. Therefore, the control unit can output voltages with relatively high levels.

In addition, while a body fat measuring function is executed by the first to fourth electrodes 311, 312, 313 and 314, the first and second antenna units 111a and 111b can perform wireless communications. That is, wireless signals can be received while a current flows in response to a part of the user body being brought into contact with the first to fourth electrodes 311, 312, 313 and 314. When the user's body contacts the first and second radiators 111a' 111b' or adjacent areas to the first and second radiators 111a' and 111b', noise may be generated to interfere with the communication functions of the first and second antenna units 111a and 111b.

During the execution of the body fat measuring function, the controller 180 can detect the wireless communication states through the first and second antenna units 111a and 111b and recognize a contact state between the first to fourth electrodes 311, 312, 313 and 314 and one area of the body based on changes in the detected wireless communication states. The controller 180 can provide the contact state of the one area of the body with the first to fourth electrodes 311, 312, 313 and 314 and guide information related to the user's posture based on the wireless communication states. The guide information may be implemented by visual information, audible information, vibration and the like.

Figure 2B:
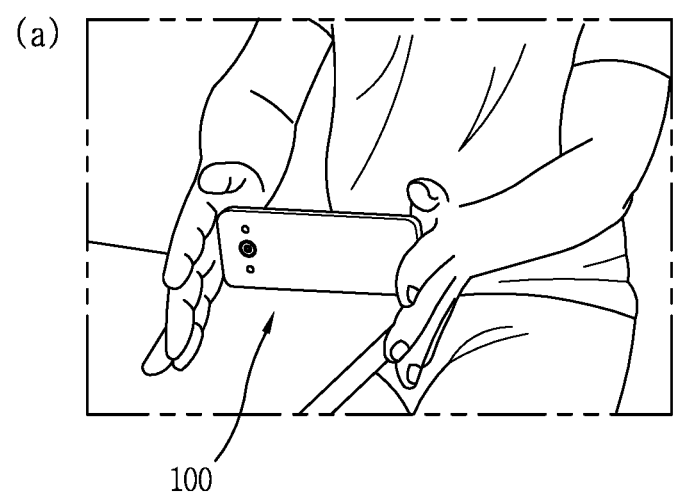
FIG. 2B is a conceptual view illustrating a method of collecting body fat information using the mobile terminal of FIG. 2A.
Figure 2B:
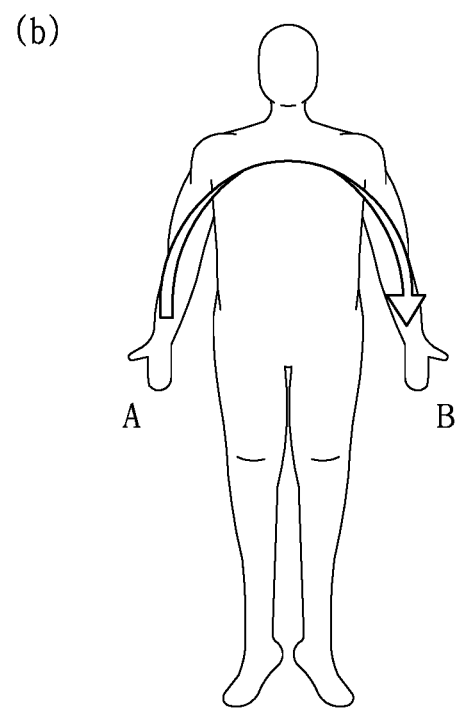

Next, FIG. 2B is a conceptual view illustrating a method of collecting body fat information using the mobile terminal of FIG. 2A. The first to fourth electrodes 311, 312, 313 and 314 are disposed on the side surfaces of the terminal body. Therefore, the user's both hands are brought into contact with the first and second electrodes 311 and 312 and the third and fourth electrodes 313 and 314, respectively. As illustrated in (b) of FIG. 2B, a current flows through the whole body based on the both hands.

Since the first to fourth electrodes 311, 312, 313 and 314 are disposed on the side surfaces of the terminal body, while the user's hands contact the electrodes, the user's hands do not obscure the display unit 151. As illustrated in (a) of FIG. 2B, the user can measure the body fat while facing the front surface of the mobile terminal 100, namely, the display unit 151. Accordingly, the user can see screen information output on the display unit 151 during the execution of the body fat measuring function.

The mobile terminal disclosed herein outputs specific screen information on the display unit 151 while the body fat measuring function is executed. Here, the specific screen information may correspond to visual information or associated with the body fat measuring function, guide information for guiding a measurement posture, a specific image which helps the user to maintain a posture, and the like.

Figure 2C:
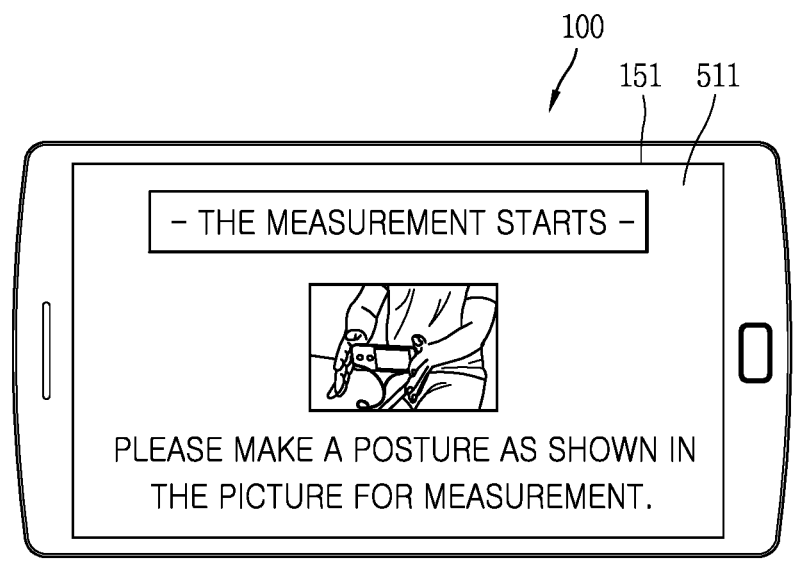
FIG. 2C is a conceptual view illustrating a control method of outputting screen information according to a function while a body fat measuring function is executed in accordance with one embodiment.
Figure 2C:
Figure 2C:
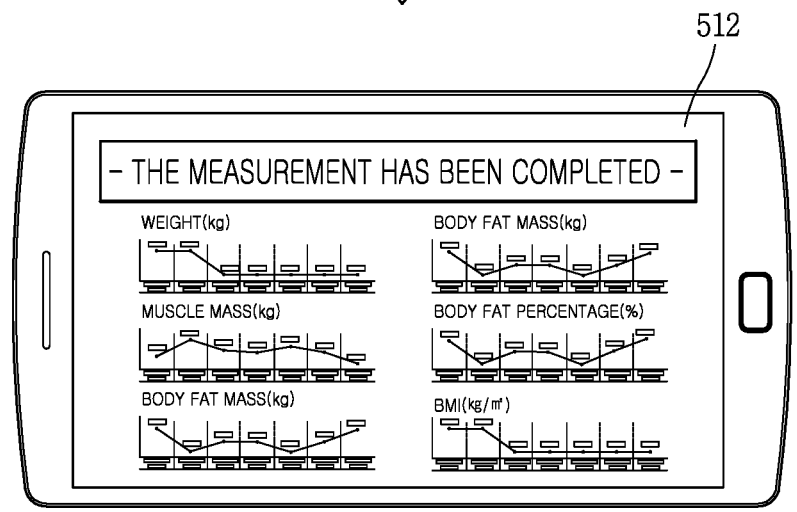

Next, FIG. 2C is a conceptual view illustrating a control method of outputting screen information according to a function while a body fat measuring function is executed in accordance with the one embodiment. The controller 180 controls the display unit 151 to output guide information 511 for guiding the measurement when the user's body is brought into contact with the first to fourth electrodes 311, 312, 313 and 314 or when the body fat measuring function is activated.

The guide information 511 includes notification information regarding the activation of the measuring function, information related to a user's measurement posture and the like. For example, the guide information 511 may include text or an image indicating a method of contacting fingers with the first to fourth electrodes 311, 312, 313 and 314, the user's posture which has to be maintained during the measurement, and the like. The guide information 511 can continuously be output while the measurement is performed. When the user's movement is sensed or the user's posture is changed during the measurement, an alarm (warning message) or the like may be output.

When body fat information is calculated in response to the completion of the measurement, the display unit 151 outputs measurement result information 512. An image notifying the completion of the measurement may also be output along with the measurement result information 512, to guide the user to change the posture and take the body away from the electrodes. According to this embodiment, while the measurement is executed, the guide information can be viewed on the display unit 151. This allows the user to maintain a proper posture during the measurement of the body fat, resulting in performing a more accurate measurement.

Figure 2D:
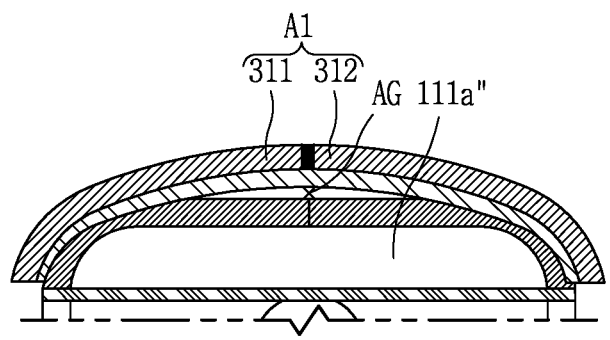
FIG. 2D is a conceptual view illustrating an arrangement of an antenna unit and an electrode unit with a gap therebetween in accordance with another embodiment.
Figure 2D:
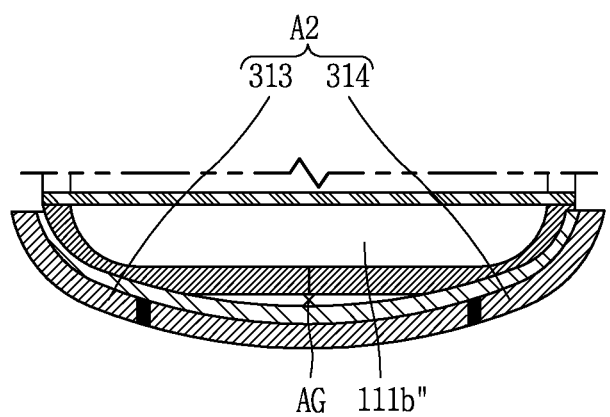

Next, FIG. 2D is a conceptual view illustrating an arrangement of an antenna unit and electrode units with a gap therebetween in accordance with another embodiment. The mobile terminal 100 disclosed herein includes the first to fourth electrodes 311, 312, 313 and 314 and first and second radiators 111a' and 111b' which are all formed on first and second functional areas A1 and A2 of the metal case. The first and second antenna units 111a and 111b respectively include first and second antenna modules 111a" and 111b" that are connected with the first and second radiators 111a' and 111b' to perform wireless communications. The antenna modules 111a" and 111b" may be disposed at both end portions of the terminal body.

Gaps AG are formed between the first and second antenna modules 111a" and 111b" and the first and second functional areas A1 and A2, respectively. The gaps AG may be filled with air or an insulating material (medium). This can prevent a degradation of antenna quality even if one area of the metal case defining the appearance of the terminal body is implemented as a radiator.

Figure 2E:
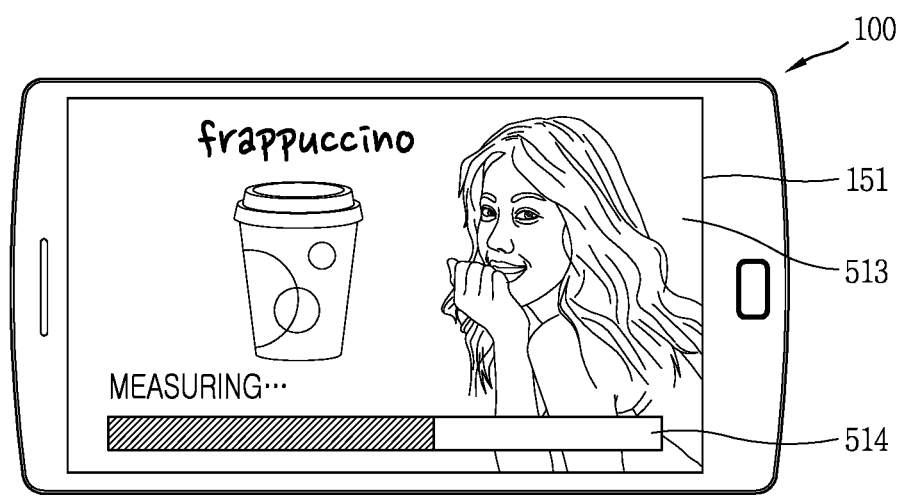
FIG. 2E is a conceptual view illustrating a control method of outputting specific screen information on a display unit in accordance with another embodiment.

FIG. 2E is a conceptual view illustrating a control method of outputting specific screen information on a display unit in accordance with another embodiment. The controller 180 can control the display unit 151 to output a preset video or image while the body fat measuring function is executed in response to one area of the user's body being brought into contact with the plurality of electrodes.

For example, the display unit 151 can output an advertisement video 513 which is reproduced for a specific time. While the advertisement video 513 is output, a progress bar 514 indicating the measurement time may also be output. The present invention is not limited to the advertisement video 513, and may alternatively include a video reproduced for a predetermined time, an image (or video) stored in the mobile terminal 100, and the like. The reproduction time of the video may be set to a time which is substantially the same as the body fat measurement time. According to this embodiment, the video is output on the display unit 151 during the execution of the body fat measuring function, which allows the user to maintain the posture for the body fat measurement time without feeling bored.

Figure 3A:
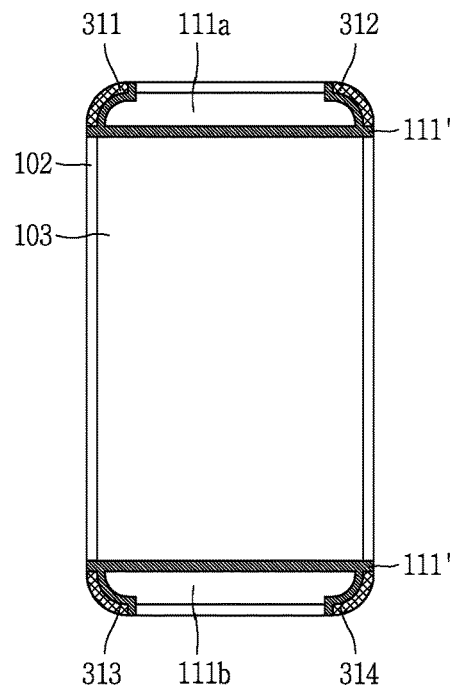
FIGS. 3A and 3B are conceptual views illustrating an arrangement of a plurality of electrodes.
Figure 3B:
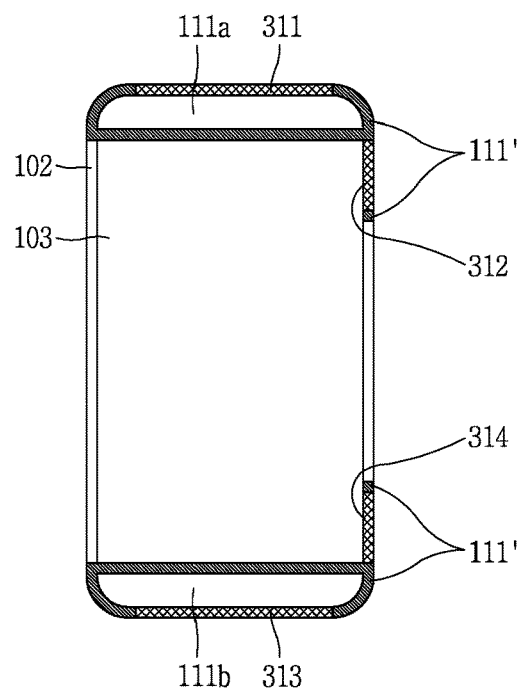

FIGS. 3A and 3B are conceptual views illustrating an arrangement of a plurality of electrodes. As illustrated in FIG. 3A, the first to fourth electrodes 311, 312, 313 and 314 may be disposed at four corners of the terminal body. The slit structures 111' are provided for insulation between the first to fourth electrodes 311, 312, 313 and 314 and a certain area of the case (the rear cover 103 and the rear case 102) which serves as the radiators of the first and second antenna units 111a and 111b. The slit structures 111' are disposed between the radiator structures forming the case and the plurality of electrodes to insulate the metal case, the electrodes and the radiator structures from one another. Size and shape of the slit structure 111' may depend on the arrangement of the electrodes.

Referring to FIG. 3B, the first and third electrodes 311 and 313 may be disposed on areas adjacent to both end portions (upper and lower portions) of the display unit 151, and the second and fourth electrodes 312 and 314 may be arranged in series on one side surface of the terminal body. The plurality of electrodes are insulated by the slit structures 111'.

Thus, the plurality of electrodes can be arranged on the side surfaces of the terminal body in various structures, so as to be configured, irrespective of the size of the terminal body, the arrangement of other electronic components, and a design of the appearance.

Figure 4A:
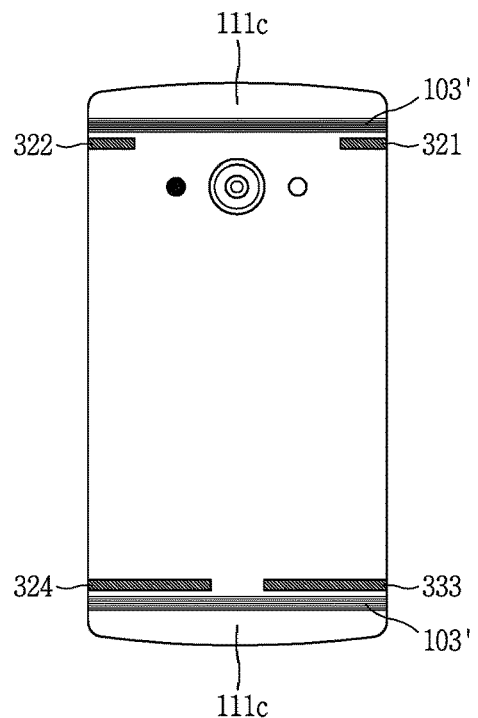
FIGS. 4A and 4B are conceptual views illustrating an arrangement of electrode units in accordance with another embodiment.
Figure 4B:
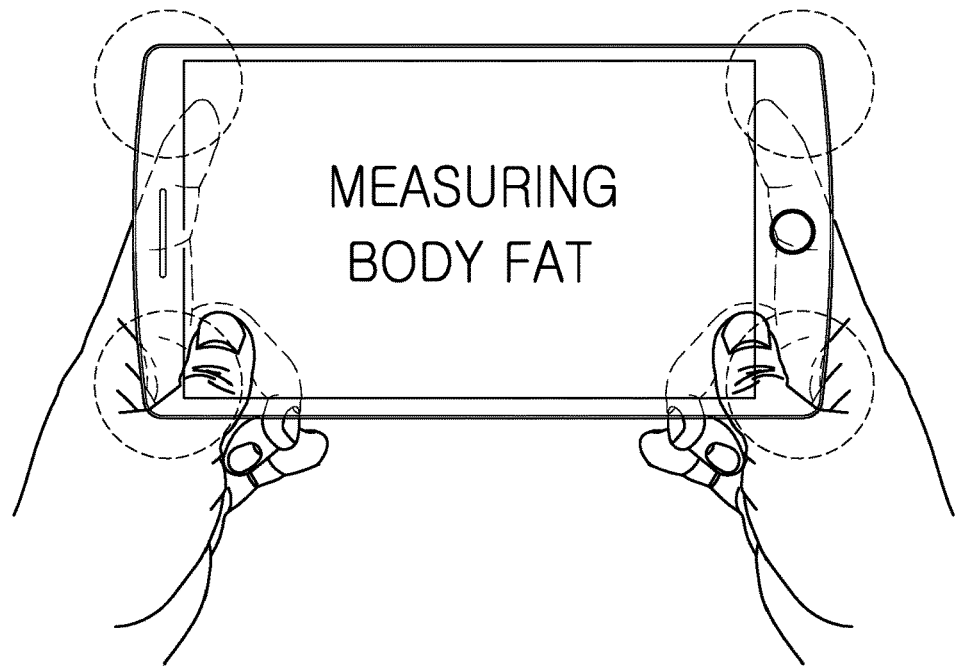

FIGS. 4A and 4B are conceptual views illustrating an arrangement of electrode units in accordance with another embodiment. The mobile terminal 100 according to an embodiment of FIG. 4A includes slot-type antenna modules 111c. Each slot-type antenna module 111c includes a radiator formed on an area of the metal case. For example, the radiator is formed of a metal on at least one area of the rear cover 103.

Both end portions of the rear cover 103 may be implemented as radiators of the slot-type antenna modules 111c, respectively. The radiators may be configured to transmit and receive different types of wireless signals. Insulating areas 103' are formed between the radiators and the other area of the rear cover 103. The insulating areas 103' according to this embodiment have a specific shape, but may alternatively be painted with substantially the same color as the other area of the rear cover 103, thereby providing a sense of unity.

First to fourth electrodes 321, 322, 323 and 324 are formed on areas adjacent to the insulating areas 103'. The first to fourth electrodes 321, 322, 323 and 324 may configure one area of the rear cover 103. In addition, additional insulating areas may be formed to insulate the first to fourth electrodes 321, 322, 323 and 324 and the other area of the rear cover 103 from each other.

The first to fourth electrodes 321, 322, 323 and 324 can have different lengths and shapes. For example, the first and second electrodes 321 and 322 may be short in length, and the third and fourth electrodes 323 and 324 may relatively be long in length. This may be set based on the arrangement of other electronic components.

Referring to FIG. 4B, while the user's thumbs support the front surface of the terminal body 100, the other fingers may be brought into contact with the first to fourth electrodes 321, 322, 323 and 324 disposed on the rear surface of the terminal body 100. Even in this instance, the display unit 151 may not be obscured in the state that the fingers contact the plurality of electrodes, which allows the user to continuously view visual information output on the display unit 151.

Figure 5A:
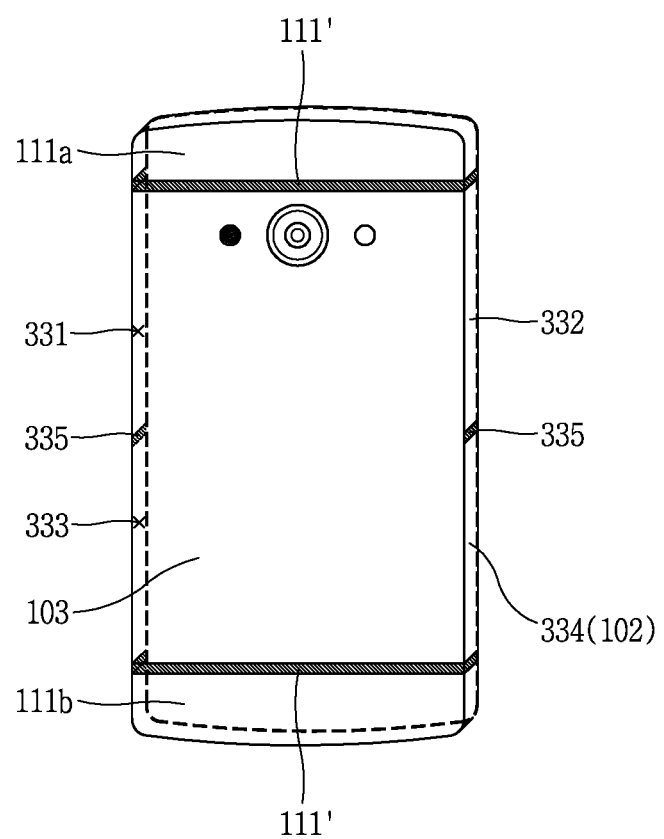
FIGS. 5A and 5B are conceptual views illustrating an arrangement of electrode units in accordance with still another embodiment.
Figure 5B:
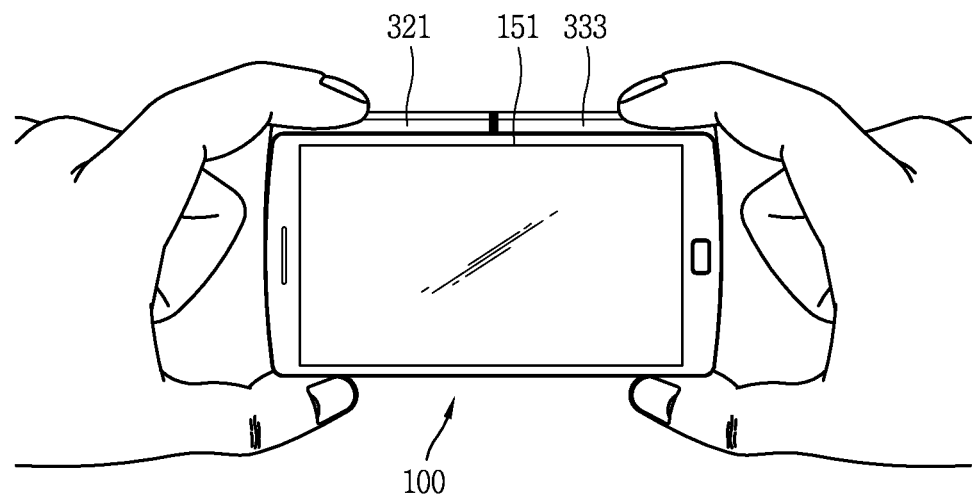

FIGS. 5A and 5B are conceptual views illustrating an arrangement of electrode units in accordance with still another embodiment. As illustrated in FIG. 5A, first to fourth electrodes 331, 332, 333, 334 are formed on the rear case 102 formed of the metal at both side surfaces of the terminal body. The first and second electrodes 331 and 332 are arranged to face each other, and the third and fourth electrodes 333 and 334 are arranged to face each other. Insulating members 335 are provided between the first and third electrodes 331 and 332 and between the second and fourth electrodes 333 and 334. Slit structures 111' are provided to insulate the first and second antenna radiators 111a and 111b and the other area of the metal case from each other.

Referring to FIG. 5B, the user contacts his/her body with the four electrodes using the fingers. Even in this instance, the display unit 151 may not be obscured by the user's fingers, and thus the user can be provided with specific screen information on the display unit 151. According to this embodiment, without using the rear cover, an area which is distinguished from the one area of the metal case serving as the radiator can be used as the electrodes. This may result in minimizing a degradation of a function of an antenna module.

Figure 6A:
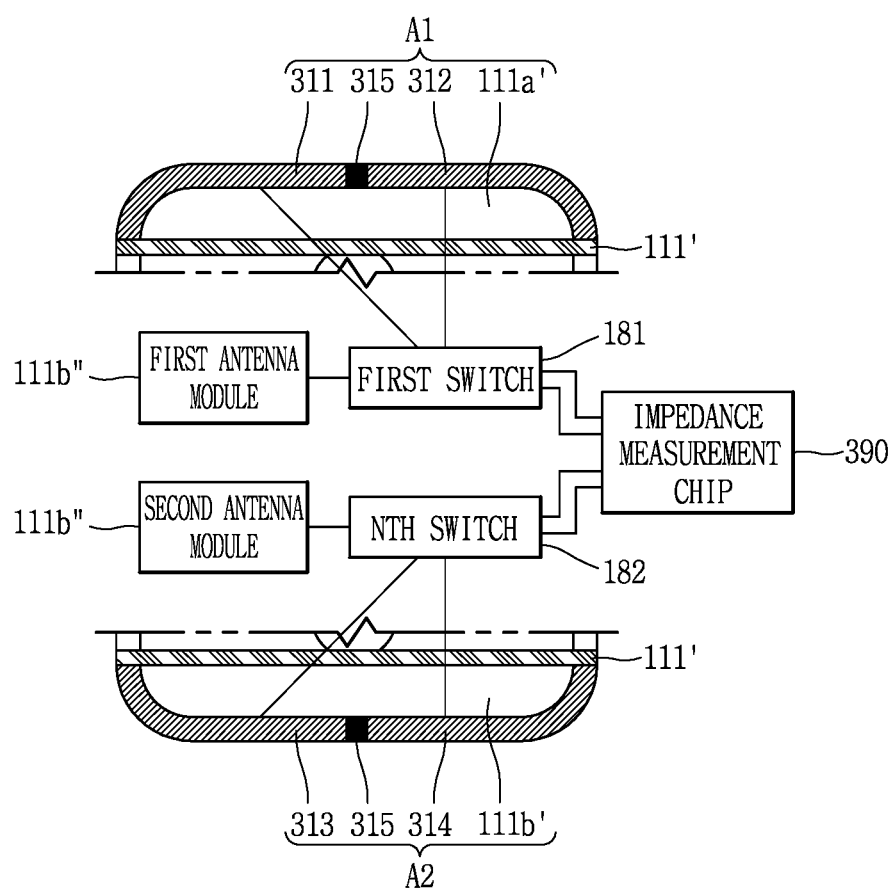
FIGS. 6A to 6C are conceptual views illustrating an arrangement of electrode units and a method of controlling a body fat measurement module in accordance with still another embodiment.
Figure 6B:
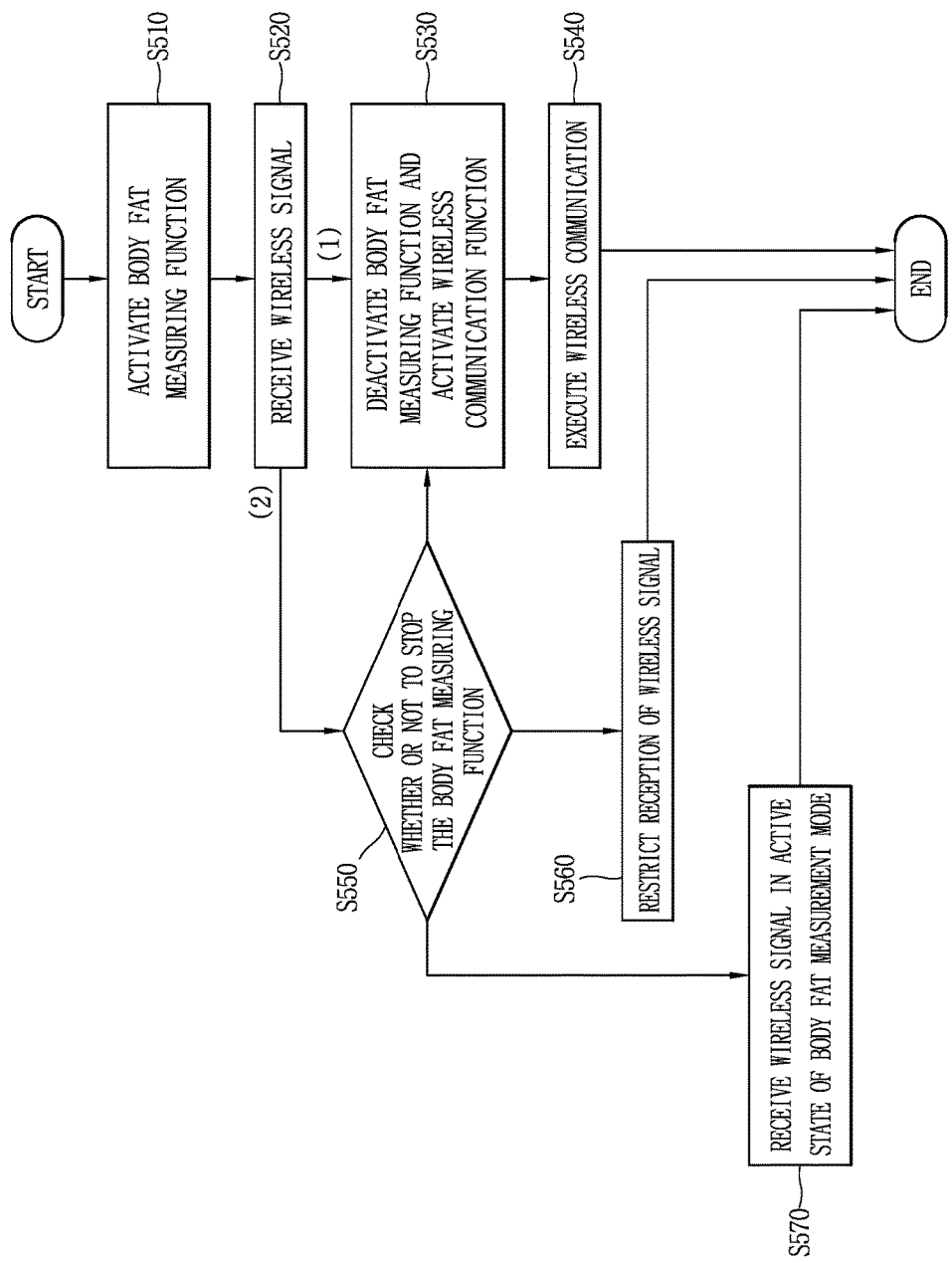

FIGS. 6A and 6B are conceptual views illustrating an arrangement of electrode units and a method of controlling a body fat measurement module in accordance with still another embodiment. In particular, FIG. 6A is a conceptual view illustrating a method of controlling the body fat measurement module and the antenna units in accordance with one embodiment.

The first to fourth electrodes 311, 312, 313 and 314 of the body fat measurement module 310 according to the embodiment of FIG. 6A have substantially the same arrangement as the first to fourth electrodes 311, 312, 313 and 314 according to the embodiment of FIG. 2A. Therefore, the same reference numerals are used and a redundant description will be omitted.

An area of the rear cover 103 and/or an area of the rear case 102 of the mobile terminal 100 according to this embodiment may be provided with the first and second radiators 111a' and 111b' of the first and second antenna units 111a and 111b, and the first to fourth electrodes 311, 312, 313 and 314. The first to fourth electrodes 311, 312, 313 and 314 and the first and second radiators 111a' and 111b' may overlap each other.

That is, one area of the case including the first and second electrodes 311 and 312 and the first radiator 111a' may be defined as a first functional area A1, and another area of the case including the third and fourth electrodes 313 and 314 and the second radiator 111b' may be defined as a second functional area A2. The first and second functional areas A1 and A2 are insulated from the other area of the case by the slit structures 111'. The insulating members 315 are disposed between the first and second electrodes 311 and 312 and between the third and fourth electrodes 313 and 314, and the slit structures 111' insulate the first and second radiators 111a' and 111b' from the other area of the case, respectively.

The first and second electrodes 311 and 312 are electrically connected with a first switch 181, and the third and fourth electrodes 313 and 314 are electrically connected with a second switch 182. The first and second switches 181 and 182 are connected with an impedance measurement chip 390 which measures impedance based on current values measured by the first to fourth electrodes 311, 312, 313 and 314.

The first and second switches 181 and 182 are connected to the first and second antenna modules 111a" and 111b", respectively. That is, the one area of the case which includes the first and second electrodes 311 and 312 and the first radiator 111a' is connected with the first switch 181 so as to be selectively connected to the first antenna module 111a" or the impedance measurement chip 390. Also, another one area of the case which includes the third and fourth electrodes 313 and 314 and the second radiator 111b' is connected with the second switch 182 so as to be selectively connected to the second antenna module 111b" or the impedance measurement chip 390. The controller 180 can selectively activate the body fat measuring function and a wireless communication function by the first and second switches 181 and 182.

Figure 6C:
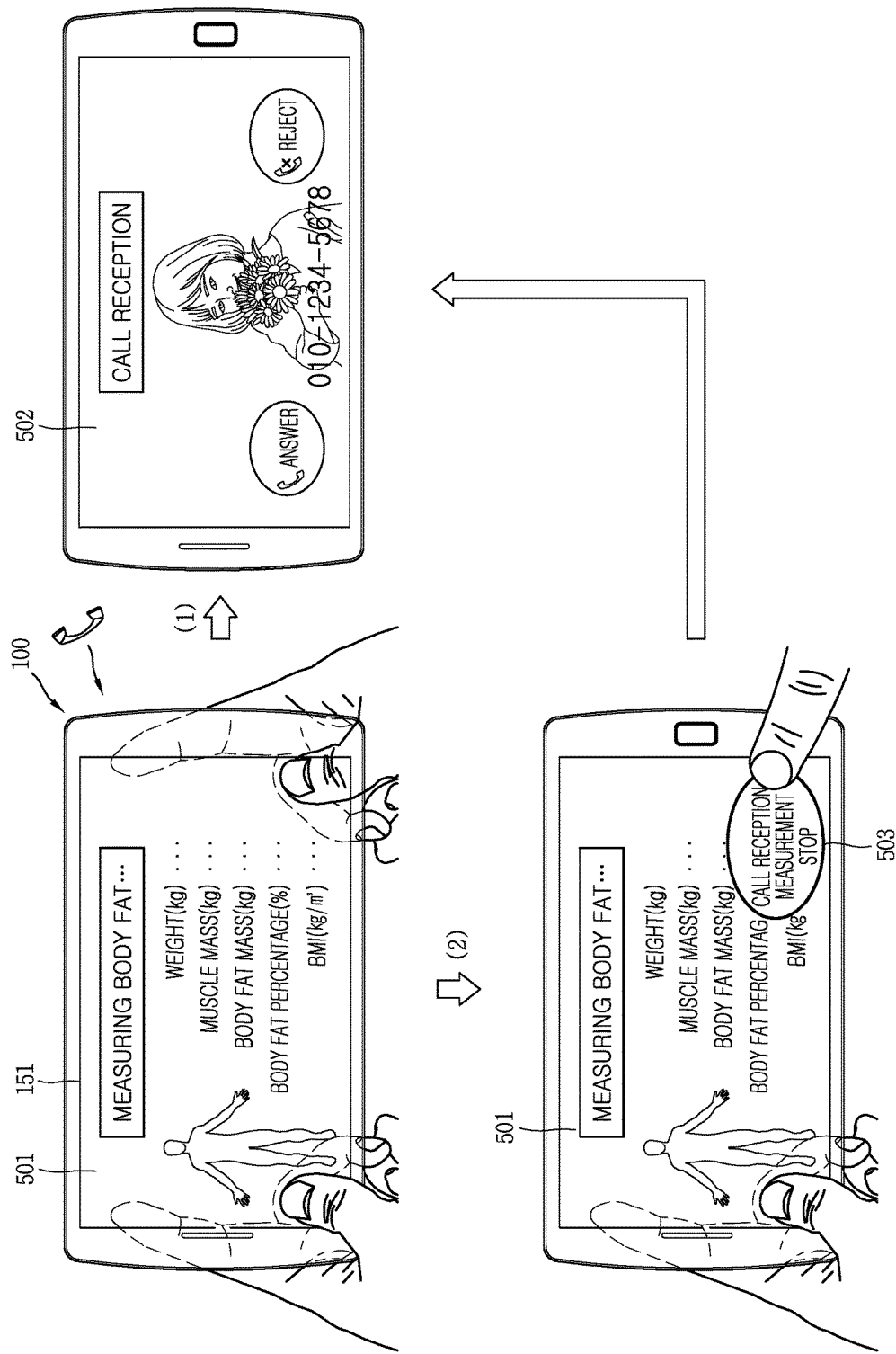

FIG. 6B is a flowchart illustrating a control method of the wireless communication function and the body fat measuring function according to the embodiment of FIG. 6A, and FIG. 6C is a conceptual view illustrating the control method of FIG. 6B. As illustrated in FIGS. 6A to 6C, the body fat measuring function is activated based on a specific control command (S510).

For example, the specific control command may be applied in response to an execution of an application associated with the body fat measuring function, or sensing of a contact between the plurality of electrodes and the user's body. However, the command for executing the body fat measuring function is not limited to this. The activation of the body fat measuring function is performed under assumption that one area of the user's body is brought into contact with all of the first to fourth electrodes 311, 312, 313 and 314.

The first and second switches 181 and 182 are converted into a first mode such that the functional areas of the case including the first to fourth electrodes 311, 312, 313 and 314 are electrically connected to the body fat measurement chip 390. In the first mode, the electric connection between the functional areas of the case and the first and second antenna modules 111a" and 111b" is restricted. A state that the body fat measuring function is activated is referred to as the first mode, and a state that the body fat measuring function is deactivated and the wireless communication function is activated by the functional areas is referred to as a second mode.

The display unit 151 outputs first screen information 501 related to the body fat measurement in the first mode. The first screen information 501 may include guide information for guiding the user's measurement posture during the execution of the body fat measuring function, or measurement result information.

While a current flows toward one area of the body which is brought into contact with the first to fourth electrodes 311, 312, 313 and 314 in response to the activation of the body fat measuring function, namely, in the first mode, the wireless signal may be received (S520). The wireless signal refers to a signal which is received through at least a part of the first and second radiators 111a' and 111b' corresponding to the one area of the metal case.

According to a first embodiment (1), when the wireless signal is received, the controller 180 deactivates the body fat measuring function and activates the wireless communication function using the first antenna unit 111a or the second antenna unit 111b (S530). For example, the wireless signal may correspond to a call signal received from an external device.

In more detail, when the wireless signal is received by the first radiator 111a' which is capable of executing the body fat measuring function, the controller 180 blocks a path connected to the impedance measurement chip 390. The controller 180 then controls the first switch 181 to electrically connect the first and second electrodes 311 and 312 to the first antenna module 111a", and controls the second switch 182 to electrically connect the third and fourth electrodes 313 and 314 to the second antenna module 111b".

The controller 180 can control a current supplied to some of the plurality of electrodes to be cut off. In addition, when a specific wireless signal is received, the controller 180 can control only one switch for receiving the specific wireless signal to convert a mode, of the plurality of switches. Even in this instance, the controller may control a current supplied to the plurality of electrodes to be temporarily cut off.

The controller 180 controls the wireless communication unit 111 to execute the wireless communication in the second mode (S540). When being converted into the second mode, the display unit 151 outputs second screen information 502 related to the received wireless signal. For example, the second screen information 502 may correspond to an execution screen of a call application associated with the received call.

According to this embodiment, when the wireless signal is received, the controller may stop the body fat measuring function even in the state that the user's body is brought into contact with the plurality of electrodes, and control the first and second functional areas A1 and A2 to be used only as the radiators for executing the wireless communication. Accordingly, noise which may be generated due to a current flowing through the first and second functional areas A1 and A2 can be minimized, thereby preventing the efficiency of the wireless communication from being lowered.

According to a second embodiment (2), when the wireless signal is received, the controller 180 checks whether or not to stop the body fat measuring function (S550). For example, the controller 180 outputs a graphic image 503, which is provided to check whether or not to stop the body fat measuring function, on the first screen information 501. The controller 180 can execute at least one of the body fat measuring function and the wireless communication function based on a touch input applied to the graphic image 503.

The graphic image 503 may include information related to the received wireless signal. According to this embodiment, the first and second switches 181 and 182 may connect the first and second functional areas A1 and A2 to all of the first and second antenna modules 111a" and 111b" and the body fat measurement chip 390, or selectively to the first and second antenna modules 111a" and 111b" or the body fat measurement chip 390.

The controller 180 can deactivate the body fat measuring function and activate the wireless communication function based on a touch input applied to the graphic image 503 (530). Or, the controller 180 can restrict the reception of the wireless signal based on a touch input applied to the graphic image 503 (S560). The controller 180 can control the first and second switches 181 and 182 to release the electric connection between the first and second functional areas A1 and A2 and the first and second antenna modules 111a" and 111b".

In this instance, the controller 180 can continuously execute the body fat measuring function, and output information related to the wireless signal in a specific manner after the completion of the body fat measuring function. In addition, the controller 180 can control the first and second switches 181 and 182 such that the wireless communication function can also be executed during the execution of the body fat measuring function, in response to a touch input applied to the graphic image 503.

According to this embodiment, when a wireless signal is received during the execution of the body fat measuring function, the received wireless signal may be checked and the wireless communication or the body fat measuring function may selectively be activated. Therefore, a more accurate body fat measurement result can be provided by temporarily stopping the wireless communication function or a wireless communication function with minimized noise can be executed. Or, both of the functions can simultaneously be executed according to a user selection even though quality is lowered. Accordingly, the wireless communication and the body fat measurement can efficiently be implemented using the metal case.

Figure 7A:
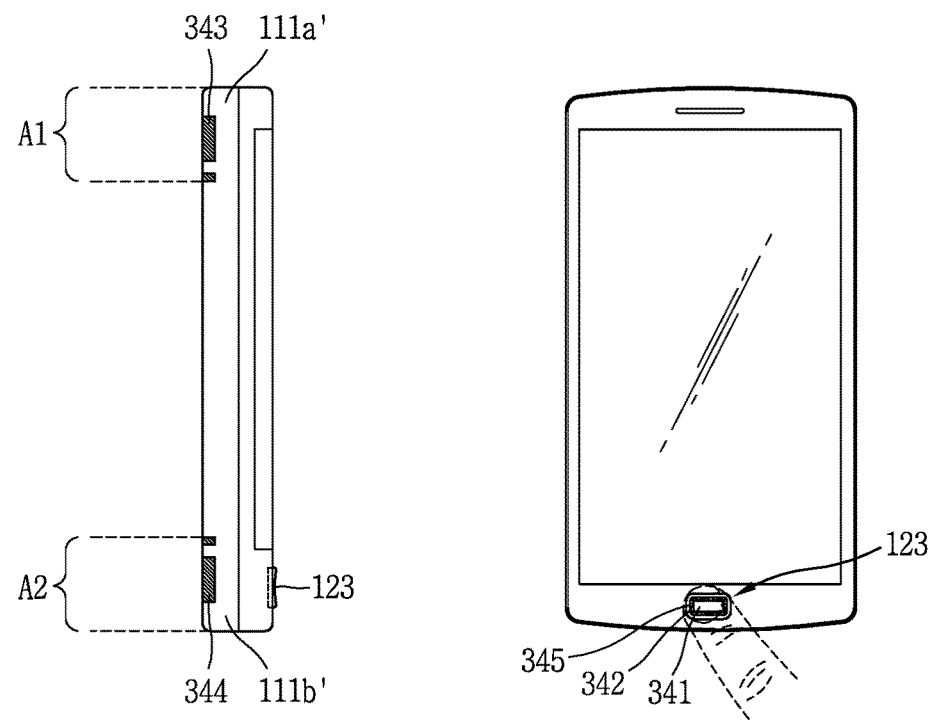
FIGS. 7A and 7B are conceptual views illustrating an arrangement of electrode units in accordance with still another embodiment.
Figure 7B:
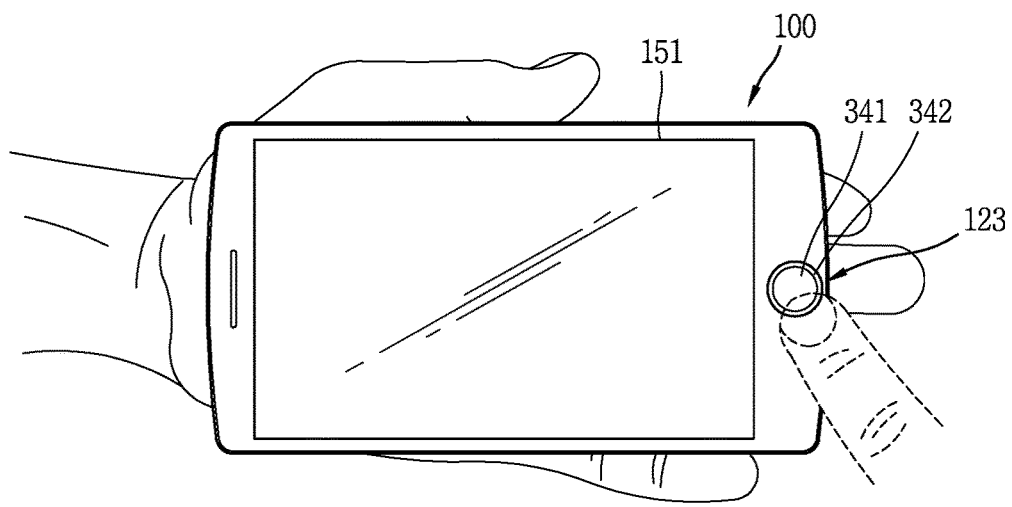

FIGS. 7A and 7B are conceptual views illustrating an arrangement of electrode units in accordance with still another embodiment. (a) of FIG. 7A is a conceptual view of the mobile terminal 100, viewed from a side surface, and (b) of FIG. 7A is a conceptual view illustrating one surface of the mobile terminal 100 on which the display unit 151 is disposed. The mobile terminal 100 includes the first and second radiators 111a' and 111b' and the third and fourth electrodes 313 and 314 provided on the first and second functional areas A1 and A2.

The mobile terminal 100 also includes the first and second electrodes 311 and 312 formed on a metal decorative portion of the signal input unit 123. The third and fourth electrodes 313 and 314 and the first and second radiators 111a' and 111b' are implemented by the one area of the case made of the metal, and insulated from each other by the insulating structures and the slit structures.

Referring to (b) of FIG. 7A, the signal input unit 123 is disposed on the front surface of the mobile terminal 100 on which the display unit 151 is disposed. The signal input unit 123 includes a first electrode 341, an insulating member 345 surrounding the first electrode 341, and a second electrode 342 surrounding the insulating member 345.

Referring to FIG. 7B, the user supports the rear surface of the mobile terminal 100 with one palm such that the fingers are brought into contact with third and fourth electrodes 343 and 344, and contacts the first and second electrodes 341 and 342 with another hand such that a current can flow along one area of the body.

In this instance, only some of the four electrodes share the metal area of the case with the radiator of the antenna unit provided on one surface (rear surface), and the rest of electrodes uses another surface (front surface) of the mobile terminal, which may result in minimizing an electric collision with the antenna unit. Also, during the execution of the body fat measurement, the user's hands may not interfere with the display unit 151 and thus the user can continuously view screen information.

Figure 8A:
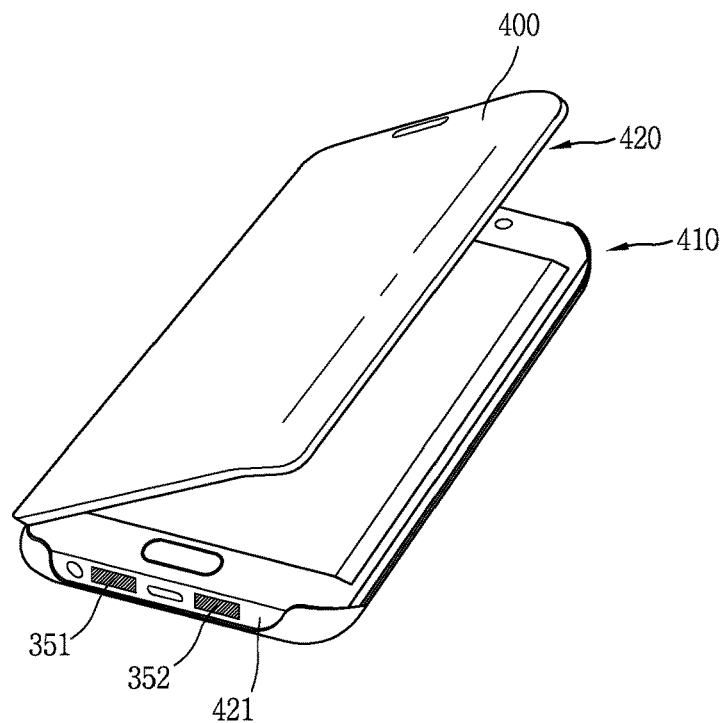
FIGS. 8A and 8B are conceptual views illustrating an arrangement of electrode units included in a mobile terminal with a cover device in accordance with one embodiment of the present invention.
Figure 8B:
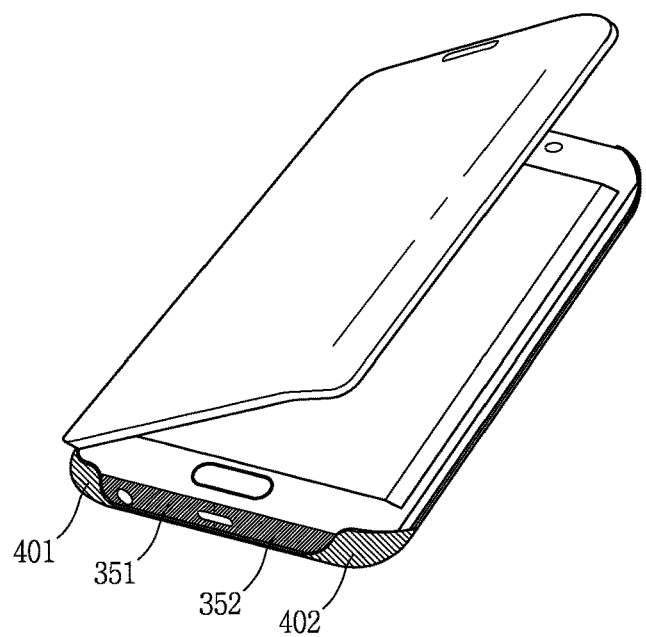

FIGS. 8A and 8B are conceptual views illustrating an arrangement of electrode units included in a mobile terminal with a cover device in accordance with one embodiment of the present invention. As illustrated in FIG. 8A, a cover device 400 may include first and second cover members 410 and 420 that are relatively rotatable away from each other. The first cover member 410 is mounted on the rear cover 103 of the mobile terminal 100 or mounted in replacement of the rear cover 103. The second cover member 420 is connected to the first cover member 410 to open and close the display unit 151.

When first and second electrodes 351 and 352 of a plurality of electrodes are formed on one side surface of the terminal body, the first cover member 410 includes an open area formed on an area corresponding to the first and second electrodes 351 and 352. According to this embodiment, the first and second electrodes 351 and 352 can be externally exposed even when the cover device 400 is coupled to the terminal body, and thus the body fat measuring function can be executed even without separating the cover device 400 from the terminal body.

Referring to FIG. 8B, when the first and second electrodes 351 and 352 are formed on one side surface of the terminal body, electrode areas may be formed on one area of the first cover member 410 and/or one area of the second cover member 420. For example, the first cover member 410 may include first and second electrode areas 401 and 402 which are formed to overlap at least part of the first electrode 351 and at least part of the second electrode 352, respectively.

Accordingly, when the user's body is partially brought into contact with the electrode areas in the state that the cover device 400 is coupled to the terminal body, a current may flow due to the electrode areas and the electrodes, thereby enabling the execution of the body fat measuring function.

Figure 9A:
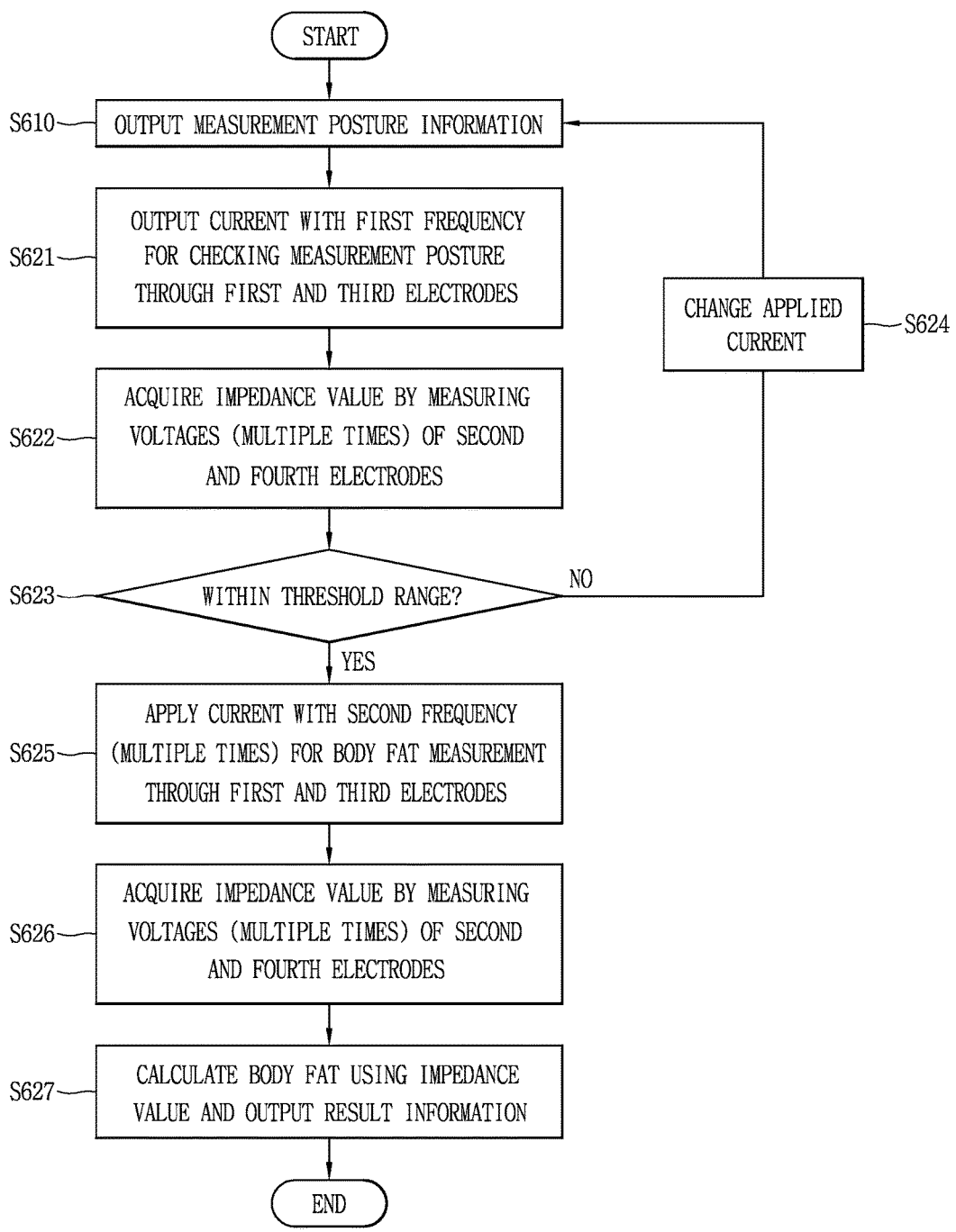
FIGS. 9A to 9C are conceptual views illustrating a control method of measuring body fat in accordance with various embodiments.
Figure 9B:
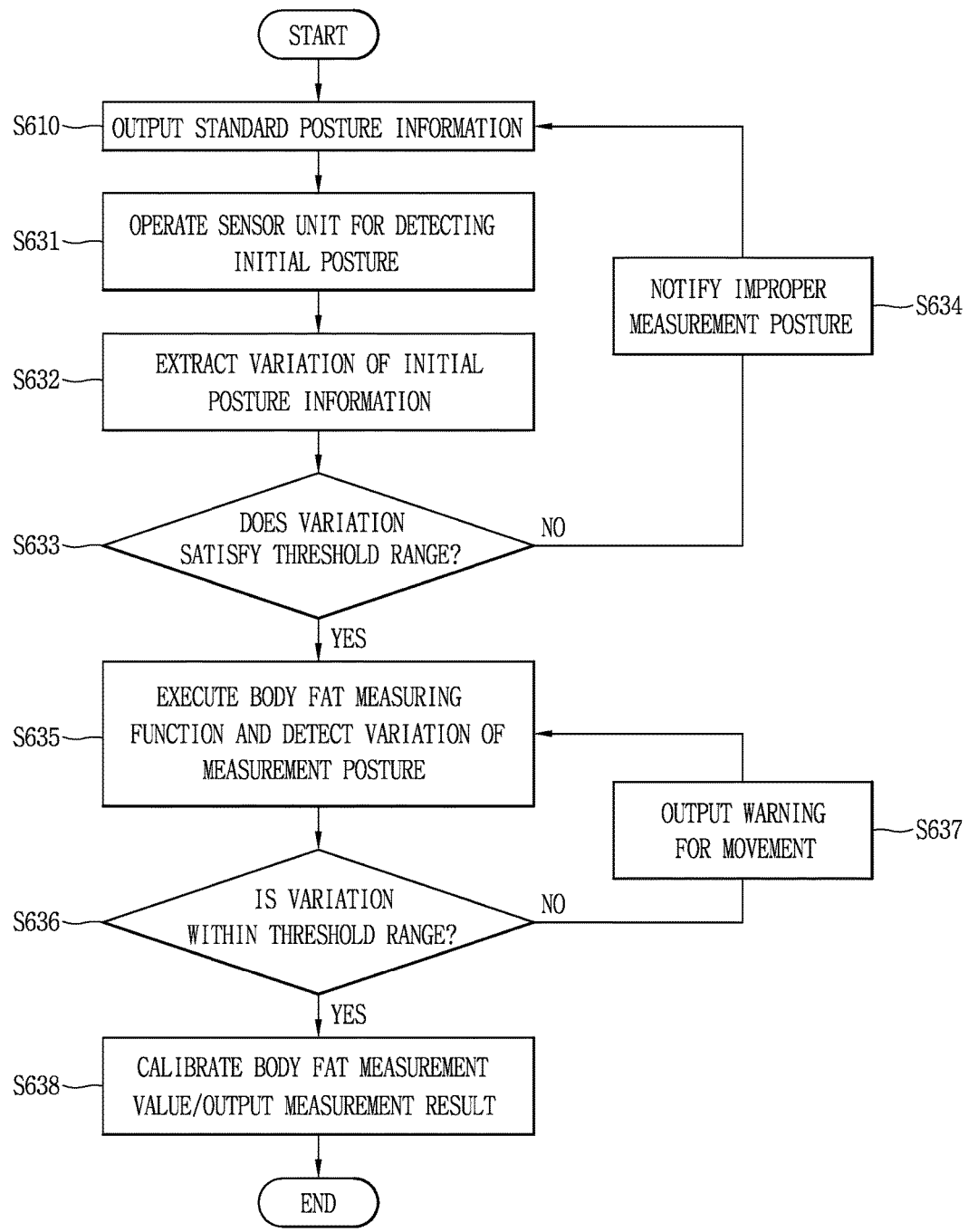
Figure 9C:
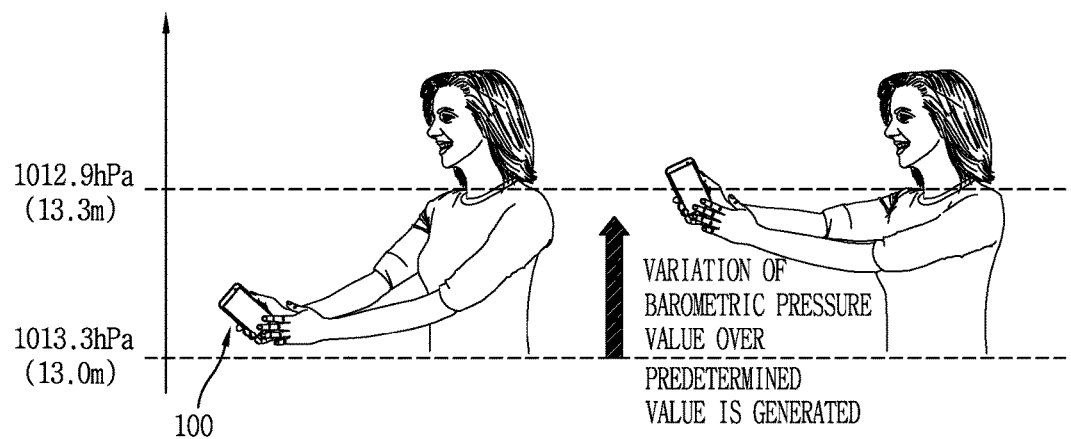
Figure 9C:
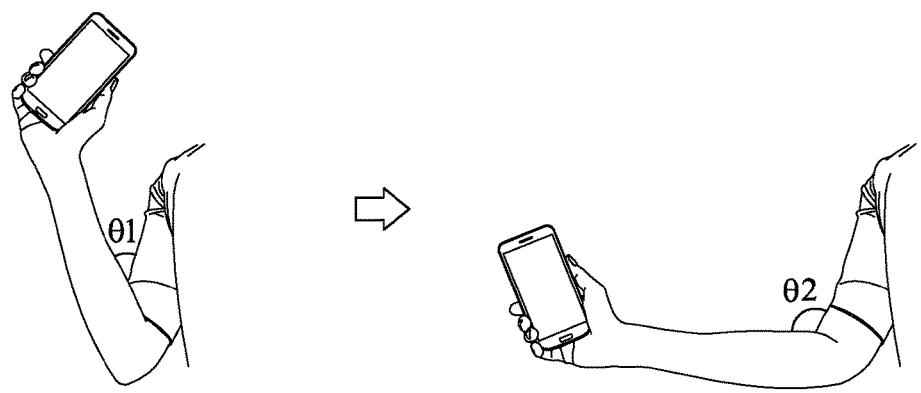

FIGS. 9A to 9C are conceptual views illustrating a control method of measuring body fat in accordance with various embodiments. FIG. 9A is a flowchart illustrating a control method of measuring body fat by supplying a current with a frequency, which is appropriate for a user, through a plurality of electrodes.

Referring to FIGS. 2A and 9A, the controller 180 outputs measurement posture information (S610). The measurement posture information may be implemented as visual information or audible information. For example, the display unit 151 may output an image or text indicating a correct measurement posture. Or, the audio output module 152 may output voice information describing a correct measurement posture. The controller 180 outputs the measurement posture information for a specific period of time. The user may make one area of the user's body brought into contact with the plurality of electrodes in the correct posture while the measurement posture information is output.

The controller 180 outputs a current with a first frequency for checking the measurement posture through the first and third electrodes 311 and 313 while the measurement posture information is output (S621). The current with the first frequency flows through the user' body, and the controller 180 measures a difference between voltages of the second and fourth electrodes 312 and 314 so as to acquire an impedance value (S622). The step of measuring the voltages may be executed multiple times.

The controller 180 determines whether or not the acquired impedance value is within a preset threshold range (S622). Here, the threshold range may correspond to a current/voltage value which is acquired when the body fat mass of the user's body is stably calculated, and the determination may be performed based on whether or not the sensed current/voltage value forms a stable waveform.

The impedance value is calculated based on previously-input basic information (e.g., user's weight, height, age, sex, etc.) before the execution of the body fat measuring function. When the acquired impedance value is not in the threshold range, the controller 180 changes the frequency value of the applied current (S624). Simultaneous to changing the frequency value of the applied current, the controller 180 can output the measurement posture information again for inducing a correct posture.

When the acquired impedance value is within the threshold range, the controller 180 outputs a current with a second frequency for measuring the body fat through the first and third electrodes 311 and 313 (S625). Or, the controller 180 can compare an impedance value acquired when the current with the first frequency is applied through the first and third electrodes 311 and 313 with an impedance value acquired when the current with the first frequency is applied through the second and fourth electrodes 312 and 314. When the former and latter impedance values are calculated substantially the same as each other, it may be determined that the measurement posture is stable and thus a current with a frequency for the body fat measurement is output.

The controller 180 acquires an impedance value by measuring voltages of the second and fourth electrodes 312 and 314 (S626), and outputs measurement result information by calculating the body fat using the impedance value (S627). According to this embodiment, whether the user's body appropriately contacts the electrodes and whether or not the user takes a correct posture in order to measure an accurate body fat can be recognized based on the acquired impedance value, without a separate sensor.

FIG. 9B is a flowchart illustrating a control method of executing the body fat measuring function by detecting a change of a user's posture. Referring to FIGS. 2A and 9A, the controller 180 outputs standard posture information for a preset time (S610), and activates a sensor unit for sensing an initial posture (S631). The sensor unit includes at least one of an acceleration sensor, a gyro sensor, a geomagnetic sensor, and a barometric pressure sensor, so as to sense a tilt and a position of the mobile terminal 100.

The sensor unit detects a movement of the mobile terminal 100 to extract variation of the initial posture information while the standard posture information is output (S521). The controller 180 determines whether or not the variation of the initial posture information corresponds to a threshold range (S633). The controller 180 outputs a notification for a wrong measurement posture when the variation of the initial posture information does not correspond to the threshold range (S634).

In addition, when the variation satisfies the threshold range, the controller executes the body fat measuring function and controls the sensor unit to detect a variation of the measurement posture (S635). The controller determines whether or not the variation of the measurement posture is within a threshold range while the body fat measuring function is executed (S636).

The controller 180 outputs a notification for warning a movement when the variation of the measurement posture is not within the threshold range (S637). The warning may be output in at least one of visual, audible and vibrating manners. When the variation of the measurement posture is within the threshold range, the controller 180 calibrates the body fat measurement value using the variation of the measurement posture and outputs the measurement result (S638).

According to this embodiment, the user's correct or wrong posture can be detected through the sensor unit for measuring a correct body fat, an excessive change of the user's measurement posture can be prevented while the current for measuring the body fat is applied. Also, the variation of the measurement posture can be detected during the measurement, which allows for calculating a more accurately-calibrated measurement result.

FIG. 9C is a conceptual view illustrating a control method of executing a body fat measuring function by sensing the user's posture. Referring to (a) of FIG. 9C, the controller 180 detects a movement of the mobile terminal 100 using the sensor unit. For example, when it is detected by use of an altitude sensor and/or a barometric pressure sensor that a height of the mobile terminal 100 increases higher than a specific value (e.g., when a variation of a barometric pressure value is higher than a specific reference value), the controller 180 executes the body fat measuring function.

The specific value and the specific reference value may be set based on the user's height. According to this embodiment, a state that the user holds an arm (or arms) at a specific height may be determined as an appropriate posture to execute the body fat measuring function.

Referring to (b) of FIG. 9C, the controller 180 detects the movement of the mobile terminal using the sensor unit. When an acceleration value of the mobile terminal is more than a specific reference value, the controller 180 determines that the user's min is open wide by more than a specific angle and thus executes the body fat measuring function. Whether or not the arm has been open away from the bulk of the user's body may be determined through a sensor sensing a distance.

According to this embodiment, the body fat measuring function can be executed by determining the state that the user's arm is open by more than the specific angle as the appropriate posture, thereby calculating a more correct measurement result.

FIGS. 10A to 10D are flowcharts illustrating a control method of correcting (adjusting) a measurement posture and executing a body fat measuring function. The body fat measurement module of the mobile terminal 100 according to FIG. 10A may further include pressure sensing units that are disposed adjacent to the plurality of electrodes to sense applied pressure. For example, the pressure sensing unit may be implemented as a sensor member, such as a piezo sensor which senses external force, or as a button structure generating a signal in response to external force.

The controller 180 measures each electrode contact pressure using the pressure sensing unit (S641), and determines whether or not the measured pressure value is more than a threshold value (S642). In order to apply a current to the user's body, the user's body should be brought into contact with each of the electrodes by specific pressure. Therefore, when the measured pressure value is smaller than the threshold value, the controller 180 outputs notification information notifying a posture correction (S643). The notification information may be output in various manners.

The threshold value may be set as a pressure value which is strong enough that the user's body can be closely adhered onto the electrodes. This may be decided based on areas of the electrodes, an arrangement of the electrodes and the like.

In addition, the controller 180 starts the body fat measurement when the pressure value is more than the threshold vale (S644). Also, the controller may continuously measure the pressure value during the execution of the body fat measuring function. When the pressure value is smaller than the threshold value, the controller may output notification information to guide the user to continuously contact a part of his/her body with the electrodes.

Also, the controller may calibrate an impedance value using the sensed pressure values, thereby providing a more correct measurement result. According to this embodiment, it can be determined whether or not the user contacts his/her body with the electrodes by appropriate pressure for a correct body fat measurement, which may enable the correct body fat measurement.

Figure 10A:
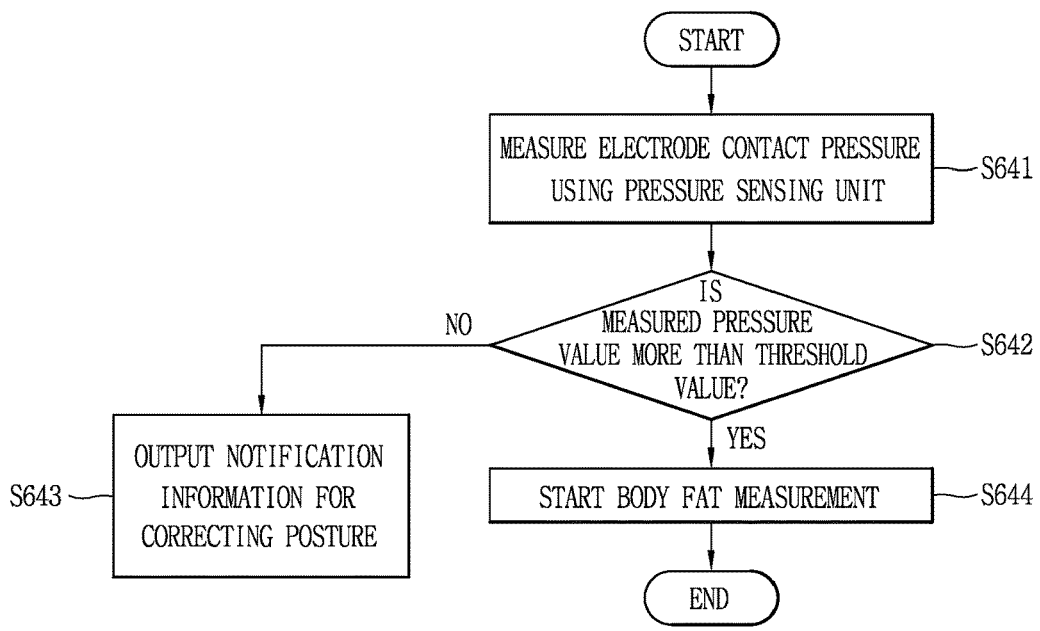
FIGS. 10A to 10D are flowcharts illustrating a control method of correcting (adjusting) a measurement posture and executing a body fat measuring function.
Figure 10B:
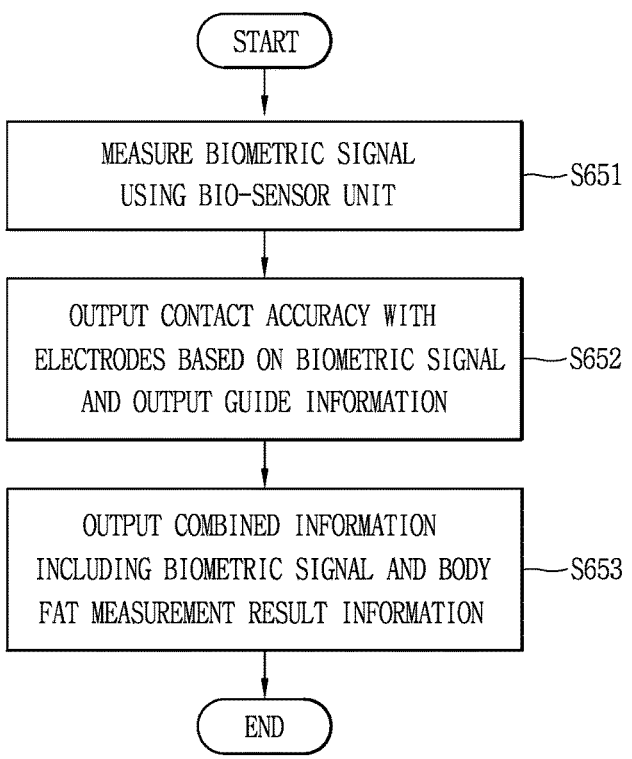

The mobile terminal 100 according to FIG. 10B further includes a bio-sensor unit collecting a biometric signal. For example, the bio-sensor unit may correspond to at least one of a bio-sensor using electrodes for measuring an electrocardiogram, an electromyogram, body temperature and the like, and a bio-sensor using an optical method for measuring a pulse wave, non-contact body temperature, fingerprint, and the like.

When the body fat measuring function is executed, the controller 180 measures a biometric signal by activating the bio-sensor unit (S651), and outputs a notification for a correct or non-correct contact with the electrodes and posture guide information based on the biometric signal (S652).

The controller 180 can continuously collect the biometric signal during the execution of the body fat measuring function. For example, for employing the bio-sensor unit using the electrodes, the biometric signal measurement may be executed while executing the body fat measurement, or performed sequential to the body fat measurement. Further, for employing the bio-sensor unit using the optical method, a measurement posture may be sensed during the execution of the body fat measuring function and the sensing result may be used for compensating for (or calibrating) the body fat measurement result.

Also, the controller 180 can detect a current user of the mobile terminal by comparing the biometric signal with pre-stored biometric data. Accordingly, the controller 180 can calculate the body fat using user information (e.g., age, height, weight, etc.) corresponding to the biometric signal.

Figure 10C:
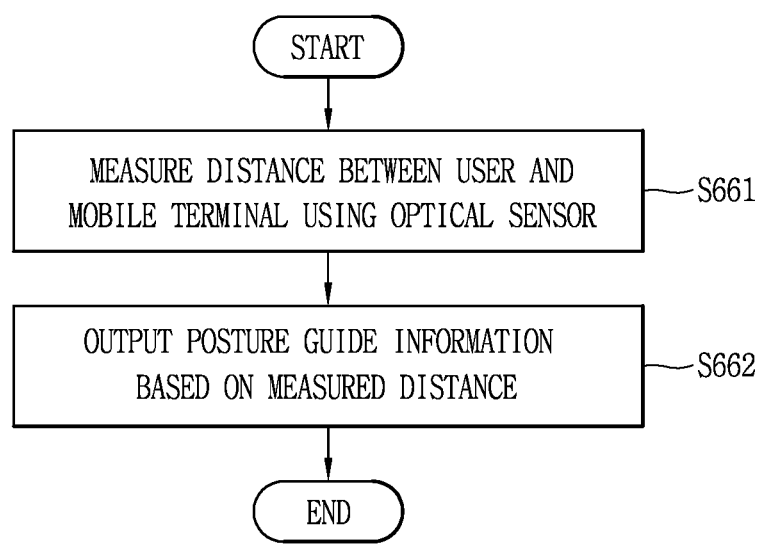

The mobile terminal 100 according to FIG. 10C include an optical sensor for measuring a distance. The optical sensor may detect a distance between the mobile terminal 100 and an object by emitting visible rays, infrared rays, far infrared rays and the like.

The controller 180 detects a distance between a user's specific body area and the mobile terminal using the optical sensor when the body fat measuring function is executed (S661). For example, when the user holds the mobile terminal 100 with a hand, the controller 180 can detect a distance between the mobile terminal 100 and the bulk of the user's body.

The controller 180 can output posture guide information based on the distance detected through the optical sensor (S662). The posture guide information may be output in a visual, audible or vibrating manner.

For example, when the sensed distance between the mobile terminal 100 that the user holds and the bulk of the user's body is closer than a specific reference, the controller may determine it as the user' arm being excessively folded and thus output guide information to guide the user to unfold the arm more. According to these embodiments, the mobile terminal 100 can collect various information to guide the user's posture during the body fat measurement, and can calibrate the body fat measurement result value based on the change in the posture, thereby providing a more correct measurement result.

Figure 10D:
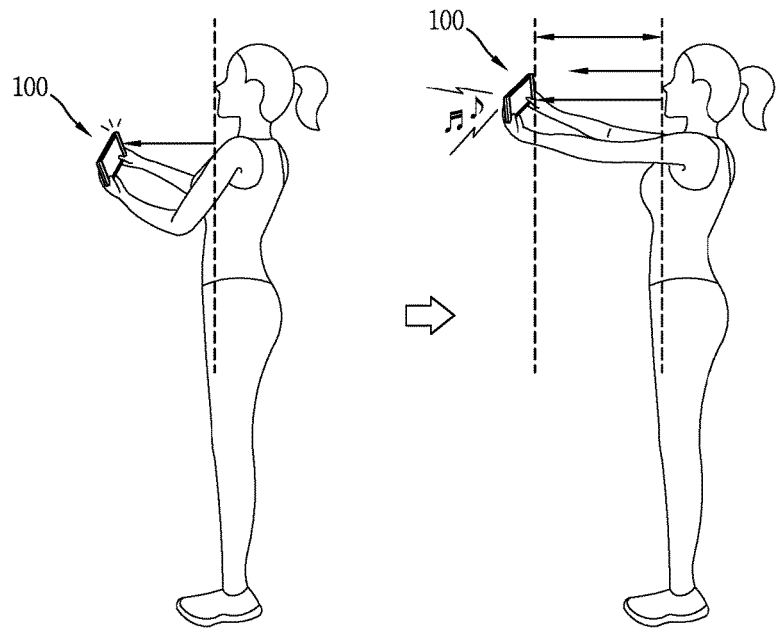
Figure 10D:
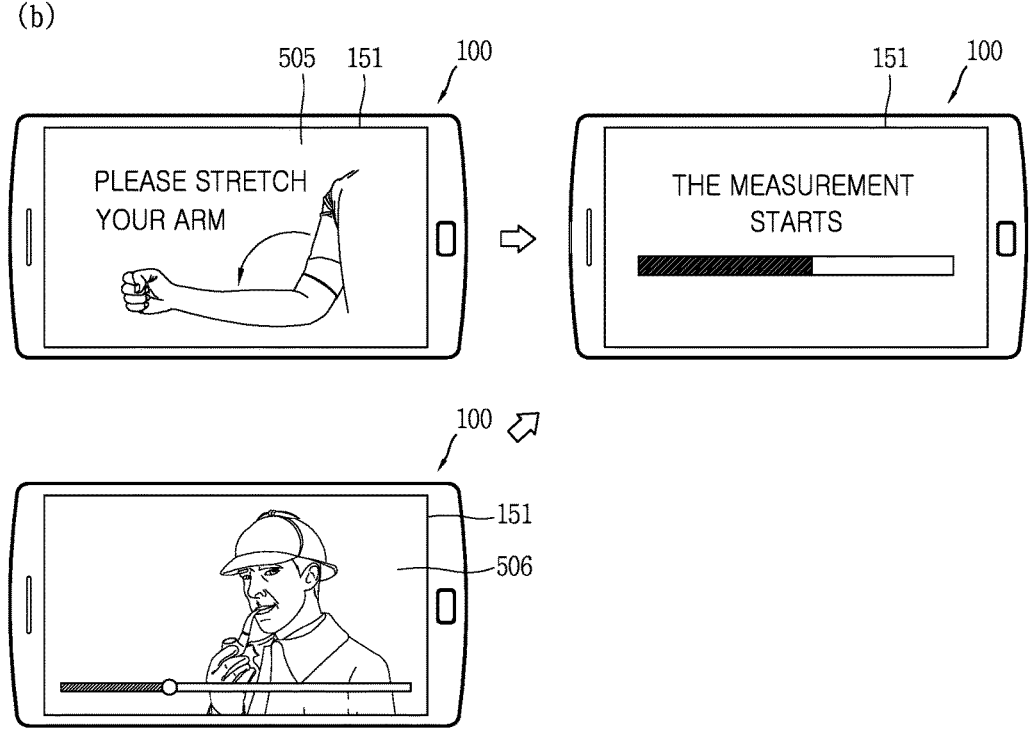

FIG. 10D is a conceptual view illustrating a control method of executing a body fat measuring function in accordance with one embodiment. The mobile terminal 100 according to this embodiment may execute the body fat measuring function by sensing a change of the user's posture. As illustrated in (a) and (b) of FIG. 10D, when the mobile terminal 100 is moved by the user, the controller 180 recognizes the movement as a control command for executing the body fat measuring function. For example, when the mobile terminal is moved faster than a specific speed due to the user suddenly stretching a folded arm, the controller 180 can execute the body fat measuring function.

For example, when one area of the user's body is brought into contact with all of the plurality of electrodes, the controller 180 can output notification information notifying a body fat measurement waiting state. The notification information may be output in a visual, audible or vibrating manner. When an idle screen 505 is output on the display unit 151, the controller 180 activates a sensor unit for detecting the movement of the mobile terminal 100. The sensor unit may include at least one of an acceleration sensor, a gyro sensor, a geomagnetic sensor and a barometric pressure sensor.

The acceleration sensor may measure a moved distance of the mobile terminal 100 due to the arm being open wide. The controller 180 can output a notification message notifying a failure of the execution of the body fat measuring function when the moved distance or speed of the mobile terminal 100 fails to reach a specific reference.

In addition, length information related to the user's arm which can be measured by the acceleration sensor can be used for calculating the body fat measurement. Or, when notification information notifying the idle state is not output or a function which was being executed is continuously executed after the notification information is temporarily output, a movement of the mobile terminal 100 may be detected. For example, when a video file 506 is currently reproduced on the display unit 151, the body fat measuring function may be executed based on the movement of the mobile terminal 100. In this instance, when the contact with the electrodes is insufficient, guide information for guiding this may be provided.

According to this embodiment, when the user has good posture for the body fat measurement by moving the mobile terminal 100, it may be determined as a control command for executing the body fat measuring function. Therefore, the user can execute the body fat measurement in the good posture.

Figure 11:
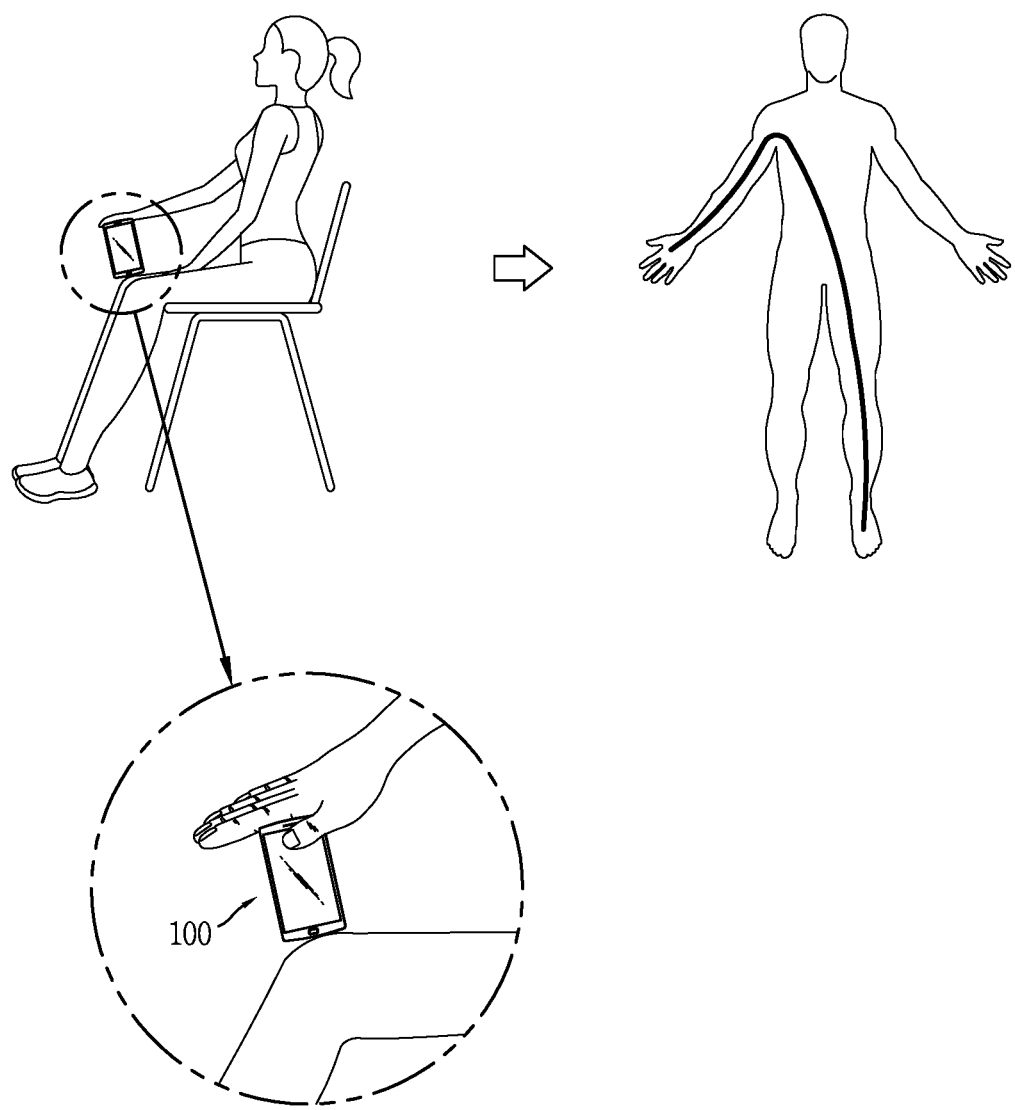
FIG. 11 is a conceptual view illustrating a control method of measuring body fat through other body areas except for hands.

FIG. 11 is a conceptual view illustrating a control method of performing a body fat measurement through other body areas except for hands. Referring to FIGS. 2A and 11, the user may contact some of the plurality of electrodes with the hand and other portion of the body. When the user contacts the plurality of electrodes with both hands, the body fat information may be calculated based on an amount of current passed through the user's upper body. However, when the user contacts the plurality of electrodes with a hand and a leg, the body fat information regarding the user's body from the upper body to a lower body can be calculated.

The controller 180 can recognize portions of the body which is brought into contact with the plurality of electrodes by detecting the position and movement of the mobile terminal 100 using the sensor unit, or allow the user to previously select a portion of the body to be brought into contact with the plurality of electrodes. Accordingly, the user can be provided with body fat measurement information regarding various body areas.

The configurations and methods of the mobile terminal in the aforesaid embodiments are not limitedly applied, but such embodiments can be configured by a selective combination of all or part of the embodiments so as to implement many variations.

The present invention can be implemented as computer-readable codes in a program-recorded medium. The computer-readable medium may include all types of recording devices each storing data readable by a computer system. Examples of such computer-readable media may include hard disk drive (HDD), solid state disk (SSD), silicon disk drive (SDD), ROM, RAM, CD-ROM, magnetic tape, floppy disk, optical data storage element and the like. Also, the computer-readable medium may also be implemented as a format of carrier wave (e.g., transmission via an Internet). The computer may include the controller 180 of the terminal. Therefore, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. A mobile terminal, comprising:
   a terminal body having a metal case and defining an appearance of the mobile terminal;
   a display disposed on one surface of the terminal body;
   an antenna having a radiator provided on a functional area of the metal case, the antenna configured to execute wireless communication;
   a plurality of electrodes provided on one portion of the functional area and configured to generate current; and
   a controller configured to:
   in response to a user grasping the mobile terminal such that the electrodes are in contact with the user, measure a body fat of the user based on voltages sensed by the electrodes, and
   display screen information on the display related to the determined body fat measurement,
   wherein a gap is formed between the antenna and the functional area, and
   wherein the gap is filled with one of air and an insulating medium.

2. The terminal of claim 1, wherein the radiator and the electrodes are provided on a common portion of the functional area.

3. The terminal of claim 2, wherein each of the electrodes includes a clad metal.

4. The terminal of claim 1, wherein the controller is further configured to display specific screen information on the display during the measurement of the body fat, and
wherein the electrodes are disposed adjacent to sides of the display.

5. The terminal of claim 1, wherein the controller is further configured to:
detect a wireless communication state of the antenna while the body fat is measured,
detect a contact state of the user grasping the mobile terminal including the electrodes based on the wireless communication state, and
display notification information on the display about the detected contact state.

6. The terminal of claim 4, wherein the controller is further configured to display on the display at least one of guide information for guiding a posture of the user, a body fat measurement result screen, and a preset video displayed for a body fat measurement time.

7. The terminal of claim 1, wherein the controller is further configured to temporarily stop measuring the body fat or deactivate the antenna in response to a wireless signal being received through the antenna while the body fat is being measured.

8. The terminal of claim 1, further comprising:
an impedance measurement chip connected to the electrodes and configured to acquire an impedance value; and
a switch selectively connecting the functional area to the impedance measurement chip and the antenna disposed within the terminal body.

9. The terminal of claim 1, wherein the controller is further configured to:
control the electrodes to output a current with a first frequency,
control the electrodes to output a current with a second frequency when an impedance value acquired by the current with the first frequency is within a threshold range, and
calculate the body fat based on the impedance value acquired by the current with the second frequency.

10. The terminal of claim 9, wherein the controller is further configured to control the electrodes to output a changed current value when the impedance value acquired by the current with the first frequency is not within the threshold value.

11. The terminal of claim 1, further comprising:
a sensor configured to sense at least one of a position and a movement of the mobile terminal, and a distance between the mobile terminal and the user,
wherein the controller is further configured to execute a body fat measuring function for measuring the body fat when a change of a posture of the user detected by the sensor satisfies a preset threshold range.

12. The terminal of claim 11, wherein the controller is further configured to output guide information for guiding the posture of the user based on the position and movement of the mobile terminal and the distance between the mobile terminal and the user sensed by the sensor.

13. The terminal of claim 11, wherein the sensor is further configured to collect sensing information during the execution of the body fat measuring function, and
wherein the controller is further configured to calibrate a body fat measurement result based on the sensing information.

14. The terminal of claim 1, further comprising:
a bio-sensor configured to detect a biometric signal of the user,
wherein the controller is further configured to:
detect a body contact state of the user with the electrodes and a posture of the user based on the biometric signal detected by the bio-sensor unit, and
measure the body fat based on the detected body contact state and the posture of the user.

15. The terminal of claim 1, wherein the terminal body comprises a front surface with the display, a rear surface and side surfaces, and
wherein the electrodes are disposed on the side surfaces.

16. The terminal of claim 1, wherein the terminal body comprises a front surface with an input unit generating a control command, a rear surface and side surfaces, and
wherein some of the electrodes are disposed on the rear surface, and the rest of the electrodes are disposed on the input unit.

17. The terminal of claim 1, wherein the electrodes and the radiator are insulated by a slit structure.

18. A method of controlling a mobile terminal including a terminal body having a metal case and defining an appearance of the mobile terminal; a display disposed on one surface of the terminal body; an antenna having a radiator provided on a functional area of the metal case, the antenna configured to execute wireless communication; and a plurality of electrodes provided on one portion of the functional area and configured to generate current, the method comprising:
in response to a user grasping the mobile terminal such that the electrodes are in contact with the user, measuring, via a controller of the mobile terminal, a body fat of the user based on voltages sensed by the electrodes; and
displaying screen information on the display related to the determined body fat measurement,
wherein the controller temporarily stops measuring the body fat or deactivates the antenna in response to a wireless signal being received through the antenna while the body fat is being measured.

19. The method of claim 18, wherein the radiator and the electrodes are provided on a common portion of the functional area.

* * * * *